United States Patent [19]
Fahy

[11] Patent Number: 5,856,081
[45] Date of Patent: *Jan. 5, 1999

[54] COMPUTER CONTROLLED CRYOPROTECTANT PERFUSION APPARATUS

[75] Inventor: Gregory M. Fahy, Gaithersburg, Md.

[73] Assignee: The American National Red Cross, Washington, D.C.

[ * ] Notice: The term of this patent shall not extend beyond the expiration date of Pat. No. 5,472,876.

[21] Appl. No.: 478,529

[22] Filed: Jun. 7, 1995

Related U.S. Application Data

[63] Continuation-in-part of Ser. No. 375,469, Jan. 19, 1995, Pat. No. 5,472,876, which is a continuation of Ser. No. 29,432, Mar. 10, 1993, abandoned, which is a division of Ser. No. 725,054, Jul. 8, 1991, Pat. No. 5,217,860.

[51] Int. Cl.$^6$ ........................................ A01N 1/02
[52] U.S. Cl. ..................... 435/1.2; 435/1.3; 435/284.1
[58] Field of Search ........................ 435/1.1, 1.2, 1.3, 435/284.1, 286.1, 286.5

[56] References Cited

U.S. PATENT DOCUMENTS

| | | | |
|---|---|---|---|
| 3,639,084 | 2/1972 | Goldhaber | 435/283 |
| 3,753,865 | 8/1973 | Belzer et al. | 435/283 |
| 3,772,153 | 11/1973 | De Rassart | 435/283 |
| 3,843,455 | 10/1974 | Bier | 435/283 |
| 3,892,628 | 7/1975 | Thorne et al. | 435/283 |
| 3,914,954 | 10/1975 | Doerig | 62/306 |
| 3,995,444 | 12/1976 | Clark et al. | 435/283 |
| 4,494,385 | 1/1985 | Kuraoka et al. | 435/1.3 |
| 4,559,298 | 12/1985 | Fahy | 435/1 |
| 4,618,586 | 10/1986 | Walker | 435/1 |
| 4,629,686 | 12/1986 | Gruenberg | 435/1 |
| 4,704,029 | 11/1987 | Van Heuvelen | 436/95 |
| 4,837,390 | 6/1989 | Reneau | 435/283 |
| 5,003,787 | 4/1991 | Zlobinsky | |
| 5,051,352 | 9/1991 | Martindale et al. | 435/283 |
| 5,141,847 | 8/1992 | Sugimachi et al. | 435/1 |
| 5,338,662 | 8/1994 | Sadri | 435/1 |
| 5,472,876 | 12/1995 | Fahy | 435/284.1 |

FOREIGN PATENT DOCUMENTS

| | | |
|---|---|---|
| 0 096 997 | 12/1983 | European Pat. Off. . |
| 2 226 482 | 1/1973 | Germany . |
| 3808942 | 9/1989 | Germany . |
| WO 93/00808 | 1/1993 | WIPO . |
| WO 94/06292 | 3/1994 | WIPO . |
| WO 96/05727 | 2/1996 | WIPO . |

OTHER PUBLICATIONS

McGraw et al. "Simple Programmable Apparatus for Enzymatic DNA Amplification". DNA and Protein Engineering Techniques. vol. 1 (1988), pp. 65–67.

(List continued on next page.)

*Primary Examiner*—William H. Beisner
*Attorney, Agent, or Firm*—Oliff, Berridge, PLC

[57] ABSTRACT

The present invention is directed to a computer controlled apparatus for perfusing, cooling, and warming a biological organ. The apparatus includes a programmable computer, selectively addressable arterial perfusate reservoirs having inputs and outputs in a recirculating fluid flow path, a main pump in the recirculating flow path for recirculating the fluid in said path, an organ pump that withdraws fluid from the recirculating fluid flow path and provides it to one or more organs in an organ flow path for subsequent return to the recirculating fluid flow path or discard, a temperature-controlled cabinet housing most components of the apparatus, and improvements that permit organ perfusion at temperatures below −10° C., immersion cooling of the organ to allow organ temperature reduction to below −40° C. to −140° C., immersion warming of the organ, and elimination of stagnant fluid in the organ flow path by means of an organ bypass valve. The apparatus may be simplified to be used exclusively for cooling on the one hand or for warming on the other. Cooling is normally accompanied by the introduction of cryoprotective agents at sub-zero temperatures, and warming is normally accompanied by the partial or complete removal of these agents.

23 Claims, 14 Drawing Sheets2

OTHER PUBLICATIONS

Torgensen et al. "Low Cost Apparatus for Primer–Directed DNA Amplification . . . ". Analytical Biochemistry. vol. 176 (1989), pp. 33–35.

M. G. O'Callaghan et al.. "An Organ Cryopreservation Apparatus", *IEEE Transaction on Biomerical Engineering,* vol. BME–24, No. 2, (1977).

Adem et al., *J. Biomed. Engineering,* vol. 3, pp. 134–139, 1981.

Armitage et al., *Cryobiology,* vol. 18, pp. 370–377, 1981.

Belzer et al., *Organ Perfusion and Preservation* (J.C. Norman et al, editors), Appleton–Century–Crofts, New York, pp. 3–12, 1986.

Fahy, G.M., "Slide Shown in 1985", (Slide of Perfusion Apparatus and Others Shown Publicaly at a Conference, 1985.

Fahy, G.M., *Cryo–Letters*, vol. 1, pp. 312–317, 1980.

Fahy, G.M., *Cryo–Letters,* vol. 5, pp. 33–46, 1984.

Fahy et al., *Crybiology,* vol. 21, pp. 407–426, 1984.

Fahy et al., *Crybiology,* vol. 22, pp. 607–608, 1985.

Jacobsen et al., *Crybiology,* vol. 15, pp. 18–26, 1978.

Jacobsen IB A., *Crybiology,* vol. 15, pp. 302–311, 1978.

Pegg, D.E., *Current Trends in Crybiology,* "Banking of Cells, Tissues and Organs at Low Temperatures", A.U. Smith editor, Plenum Press, NY, pp. 153–180, 1970.

Pegg, D.E., *Cryobiology,* vol. 9, pp. 411–419, 1972.

Pegg, D.E., *Cryobiology,* vol. 14, pp. 168–178, 1977.

Sadri, F. *T.O.P.S. Medical Corp.,* "Organ Perfusion Systems: An Evaluation Criteria", 1987.

Sherwood et al., *Organ Preservation,* Churchill Livingstone, London, Chapter 15, pp. 152–174, 1973.

Water Instruments Medical Group, Water Instruments Inc., *Price List,* 1982.

COMPUTER CONTROLLED CRYOPROTECTANT PERFUSION APPARATUS

CROSS REFERENCE TO RELATED PATENT/APPLICATIONS

This application is a Continuation-in-Part of co-pending application Ser. No. 08/375,469, filed Jan. 19, 1995, now U.S. Pat. No. 5,472,876, which in turn is a continuation of application Ser. No. 08/029,432, filed Mar. 10, 1993, now abandoned, which in turn is a division of application Ser. No. 07/725,054, filed Jul. 8, 1991, now U.S. Pat. No. 5,217,860.

FIELD OF THE INVENTION

This invention relates to the field of organ perfusion. More particularly, it relates to a computer controlled apparatus and method for perfusing isolated animal, and more specifically, human, organs. Still more particularly, this invention relates to an apparatus and method for introducing and removing vitrifiable concentrations of cryoprotective agents into and from isolated organs or tissues for preservation and subsequent use.

BACKGROUND OF THE INVENTION

Cryopreservation (that is, preservation at very low temperatures) of organs would allow organ banks to be established for transplant surgeons in much the same way blood banks serve the medical community today. The main difficulty with cryopreservation is that it requires the perfusion of organs with high concentrations of cryoprotective agents (water soluble organic molecules that minimize or prevent freezing injury during cooling to very low temperatures). No fully suitable equipment or process has been developed to date for carrying out this perfusion process. This has prevented the establishment of viable organ banks that could potentially save lives.

Devices and methods for perfusing organs with cryoprotectant have been described in the literature since the early 1970's. See, Pegg, D. E., Banking of Cells, Tissues, and Organs at Low Temperatures, *Current Trends in Cryobiology*, A. U. Smith, Editor, Plenum Press, New York, 1970: pp. 153–180, but particularly pages 175–177; and Pegg, D. E., Perfusion of Rabbit Kidneys with Cryoprotective Agents, *Cryobiology* 9:411–419, 1972).

In the apparatus initially described by Pegg, two perfusion circuits operated simultaneously, one with and one without cryoprotectant. Cryoprotectant was introduced and removed by abruptly switching from the cryoprotectant-free circuit to the cryoprotectant-containing circuit, then back again. The pressure was controlled by undescribed techniques, and data was fed into a data logger which provided a paper tape output which was processed by a programmable desk-top Wang calculator. The experimental results were poor. The equipment and technique described were considered inadequate by Pegg and his colleagues, who later modified them considerably.

In 1973, G. J. Sherwood and J. R. Flower, in: Organ Preservation (D. E. Pegg, editor, Churchill Livingstone, London, 1973, pp. 152–174), described four potential perfusion systems, none of which are known to have been built. The first system consisted of a family of reservoirs connected directly to the organ via a multiway valve, changes being made in steps simply by switching from one reservoir to another.

The second system created changes in concentration by metering flow from a diluent reservoir and from a cryoprotectant concentrate reservoir into a mixing chamber and then to the kidney. No separate pump for controlling flow to the kidney was included. Total flow was controlled by the output of the metering pumps used for mixing. A heat exchanger was used before rather than after the filter, and there was an absence of any arterial sensing. As will become readily apparent below, the only similarity between this system and the present invention was the use of two concentration sensors, one in the arterial line and one in the venous line of the kidney. Organ flow rate was forced to vary in order to minimize A-V concentration differences. The sensing of concentration before and after the kidney in the circuit is analogous to but substantially inferior to the use of a refractometer and a differential refractometer in the present invention. The present inventor's experience has shown that the use of a differential refractometer is necessary for its greater sensitivity. The concept of controlling organ A-V gradient by controlling organ flow is distinctly inferior to the system of the present invention.

The third system described by Sherwood et al. also lacked a kidney perfusion pump, relying on a "backpressure control valve" to recirculate perfusate from the filter in such a way as to maintain the desired perfusion pressure to the kidney. As with the second Sherwood system, the heat exchanger is proximal to the filter and no bubble trap is present. The perfusate reservoir's concentration is controlled by metered addition of cryoprotectant or diluent as in the second Sherwood system, and if flow from the organ is not recirculated, major problems arise in maintaining and controlling perfusate volume and concentration. None of these features is desirable.

The fourth system was noted by Pegg in an appendix to the main paper. In this system, perfusate is drained by gravity directly from the mixing reservoir to the kidney through a heat exchanger, re-entering the reservoir after passing through the kidney. Concentration is sensed also by directly and separately pumping liquid from the reservoir to the refractometer and back.

Modifications and additional details were reported in 1977 (Pegg, D. E., and Wusteman, M. T., Perfusion of Rabbit Kidneys with Glycerol Solutions at 5° C.). The apparatus used one mixing reservoir and one reservoir for adding glycerol concentrate or glycerol-free perfusate to the mixing reservoir to control concentration. The volume of the mixing reservoir was held constant during perfusion, necessitating an exponentially increasing rate of diluent addition during cryoprotectant washout to maintain a linear rate of concentration change. The constant mixing reservoir volume and the presence of only a single delivery reservoir also made it impossible to abruptly change perfusate concentration. All components of the circuit other than the kidney and a pre-kidney heat exchanger were located on a lab bench at ambient temperature, with the reservoir being thermostatted at a constant 30° C. The kidney and the heat exchanger were located in a styrofoam box whose internal temperature was not controlled. Despite this lack of control of the air temperature surrounding the kidney, only the arterial temperature but not the venous temperature or even the kidney surface temperature was measured. The use of a styrofoam box also did not allow for perfusion under sterile conditions. The only possible way of measuring organ flow rate was by switching off the effluent recirculation pump and manually recording the time required for a given volume of fluid to accumulate in the effluent reservoir, since there was no perfusion pump which specifically supplied the organ, unlike the present invention. Pressure was controlled, not on the basis of kidney resistance, but on the basis of the combined resistance of the kidney and a manually adjustable bypass valve used to allow rapid circulation of perfusate through the heat exchanger and back to the mixing reservoir. The pressure sensor was located at the arterial cannula, creating a fluid dead space requiring manual cleaning and potentially introducing undesired addition of unmixed dead space fluid into the arterial canmula. Pressure control was achieved by means of a specially-fabricated pressure control unit whose electrical circuit was described in an earlier paper (D. E. Pegg and C. J. Green, Renal Preservation by Hypothermic Perfusion. 1. The importance of pressure-control, *Cryobiology* 10:56–66, 1973). Arterial concentration but not venous concentration was measured. No computer control or monitoring was used. Concentration was controlled by feeding the output of the recording refractometer into a "process controller" for comparison to the output of a linear voltage ramp generator and appropriate adjustment of concentrate or diluent flow rate. Glycerol concentrations were measured manually at 5 minute intervals at both the mixing reservoir and the arterial sample port: evidently, the refractometer was not used to send a measurable signal to a recording device. Temperature and flow were recorded manually at 5 minute intervals. Arterial pressure and kidney weight were recorded as pen traces on a strip chart recorder. None of these features is desirable.

Further refinements were reported by Jacobsen, I. A., Pegg, D. E., Wusteman, M. C., and Robinson, S. M., Transplantation of Rabbit Kidneys Perfused with Glycerol Solutions at 10° C., *Cryobiology* 15:18–26, 1978. A bubble trap was added, the sample port on the kidney bypass was eliminated (concentration was measured at the distal end of the bypass line instead), and temperature was recorded as a trace on a strip chart recorder rather than manually every 5 minutes. Additionally, these authors reported that bypass concentration lagged reservoir concentration by 5 min (v. 3 min or less for arterial concentration in the present invention) and that terminal cryoprotectant concentration could not be brought to less than 70 mM after adding 5 liters of diluent to the mixing reservoir (v. near-zero terminal concentrations in the present invention using less than 3 liters of diluent and using peak cryoprotectant concentrations approximately twice those of Jacobsen et al.).

A variation on the system was also reported the same year by Jacobsen (Jacobsen, I. A., Distribution and Removal of Glycerol by Vascular Albumin Perfusion in Rabbit Kidneys, *Cryobiology* 15:302–311, 1978). Jacobsen measured but did not report air temperatures surrounding the kidney during perfusion. He reduced the mixing reservoir volume to 70 ml, which was a small fraction of the 400 ml total volume of the circuit. No electronic-output refractometer appears to have been used to directly sense glycerol concentration and control addition and washout. Instead, the calculated values of concentrate or diluent flow rate were drawn on paper with India ink and read by a Leeds and Northrup Trendtrak Programmer which then controlled the concentrate/diluent pump. Despite the low circuit volume, the minimum concentration of cryoprotectant which could be achieved was about 100 mM.

Additional alterations of the same system were reported by Armitage et al. in 1981 (W. J. Armitage, G. Matthes, and D. E. Pegg, Seleno-dl-methionine Reduces Freezing Injury in Hearts Protected with Ethanediol, *Cryobiology* 18:370–377, 1981). Essentially, the entire perfusion circuit previously used was placed into a refrigerated cabinet. Instead of a voltage ramp controller, a cam-follower was used. Again, however, it was necessary to calculate the required rates of addition of glycerol or diluent using theoretical equations in order to cut the cam properly, an approach which may introduce errors in the actual achievement of the desired concentration-time histories. Finally, a modification was made in which an additional reservoir was added to the circuit. This reservoir was apparently accessed by manual stopcocks (the mode of switching to and from this reservoir was not clearly explained), and use of the new reservoir was at the expense of being able to filter the perfusate or send it through a bubble trap. The new reservoir was not used to change cryoprotectant concentration; rather, it was used to change the ionic composition of the medium after the cryoprotectant had been added. The volume of the mixing reservoir was set at 500 ml, allowing a final cryoprotectant concentration of 40 mM to be achieved.

The circuits described above represent the current state of the art of cryoprotectant perfusion by others known to the present inventor.

An approach to organ preservation at cryogenic temperatures previously described by the present inventor involved vitrifying rather than freezing organs during cooling. Vitrification, or solidification without freezing, can be brought about in living systems by replacing large fractions of water in these systems with cryoprotective agents (also known as cryoprotectants) whose presence inhibits crystallization. Means of circumventing toxicity of concentrations up to the 8.4M concentration required for vitrification at atmospheric pressure have been described in a pending patent application by this inventor. What is lacking is a device that automates certain new steps necessary for such high concentrations to be tolerated.

Organ preservation at cryogenic temperatures would permit wastage of valuable human organs to be considerably reduced and would facilitate better matching of donor and recipient, a factor which continues to be important despite the many recent advances in controlling rejection. See, Terasaki, et al., in *Clinical Transplants*, 1992 (P. I. Terasaki; and J. M. Cecka, eds.), UCLA Tissue Typing Laboratory, 1993, pp. 501–512. A recent approach to the induction of tolerance to transplanted organs may require more time for the host immune system to be "re-educated" to accept the graft as "self", than will be available without being able to cryopreserve the cadaver organ See, Posselt, A. M., et al., *Science* 249:1293–1295 (1990); Remuzzi, G., et al., *The Lancet* 337:750–752 (1991).

One major limitation in organ cryopreservation studies has been the lack of suitable equipment for controlling perfusion parameters such as cryoprotectant concentration-time history, pressure, and temperature. Previously described standard perfusion machines are not designed for this application and are unable to meet the requirements addressed here.

The present inventor has described apparatus that overcame all of the deficiencies of the above previously known apparatus and methods. However, certain new procedures introduced by the present inventor and others have required modifications to that apparatus to add genuinely new capabilities.

SUMMARY OF THE INVENTION

The present invention is directed to a computer controlled apparatus for perfusing, cooling, and warming a biological organ. The apparatus includes a programmable computer and a plurality of arterial perfusate reservoirs, each having an input and an output. The contents of the reserviors are selectively sampled under the control of the computer. An organ container is provided for holding a biological organ. A recirculating fluid flow path connects selected outputs and the inputs of the plurality of reservoirs. An organ flow path extends from the recirculating flow path, through the organ pump, to the organ container. An organ pump is located in said organ flow path and is coupled to and controlled by the computer for withdrawing fluid from the recirculating flow path and delivering the fluid to one or more organs in the organ flow path, thereafter to the recirculating flow path and then either to one of the reservoirs or to the waste outlet, according to control instructions received from the computer. At least one low temperature bath is provided for containing fluid at a temperature within a predetermined range. A low temperature flow path selectively connects the low temperature bath to one or both of the flow paths upstream of the organ container. The flow of fluid in the low temperature flow path is controlled also between the low temperature bath and an outer jacket of the organ container which is used to cool the organ container. A main pump is interposed in the recirculating flow path and optionally is coupled to and controlled by the computer for circulating perfusate from a selected reservoir through the recirculating fluid flow path, as determined by control instructions received from the computer. Perfusate is selectively returned to a selected one of the reservoirs from the recirculating flow path or to a waste outlet as a function of information sensed by at least one of the sensors. A temperature-controlled cabinet houses the reservoirs, flow paths and pumps to maintain organ and perfusate temperatures at desired levels. Organ temperature can also be changed by automated immersion means including means capable of cooling organs to below −40° C. to −60° C.

FEATURES AND ADVANTAGES OF THE INVENTION

This invention has a multitude of features and advantages, among the most important of which are:

1. It permits control of the concentration of cryoprotectant or any other fluid or drug in the perfusate of an organ according to a wide variety of predetermined concentration-time histories, more or less independently of the flow rate of perfusate through the organ, with provision for simultaneously varying the concentrations of other drugs or osmotic agents. Step changes in concentration are possible, and it is possible to bring concentrations effectively to zero.

2. It provides for in-line sensing of concentration, pH, perfusate temperature, and other parameters so as to avoid the need for sensors in the perfusate reservoirs and for manual measurements.

3. It permits minimizing differences between the concentration of cryoprotectant monitored and the concentration of cryoprotectant in the perfusate reservoirs by minimizing the time required for perfusate to travel from the reservoirs to the perfusate sensors and back to the reservoirs.

4. It permits minimizing differences between the concentration of cryoprotectant monitored and the concentration of cryoprotectant actually perfused into the organ by minimizing the time required for perfusate to travel from the main fluid circuit to the perfused organ (or superfused tissue).

5. It permits monitoring of the arterio-venous difference in cryoprotectant concentration across the organ as an index of the degree of, or opportunity for, organ equilibration with cryoprotectant.

6. It permits control of the temperature of the organ essentially independently of flow through the organ, and permits varying this temperature at will.

7. It protects against perfusion of unmixed solution and air (bubbles) into the organ.

8. It interfaces with a computer to control the perfusions, to provide real-time monitoring, display, processing, and recording of the data, to calibrate the sensors and pumps, and to direct the cleaning, disinfection, and priming of the perfusion circuit and to instruct and alert the operator when necessary.

9. It permits control of the perfusion pressure, either keeping it fixed or changing it as desired, and if desired minimizing pulsation. Because pressure is controlled by a programmable computer, any pressure-time history desired can be applied. In a best mode process, in fact, pressure during deep subzero perfusion differs from the pressure used at higher temperatures (above −10° C. to −3° C.).

10. It is capable of introducing cryoprotective agents (CPA) in stages, including some CPA near 0° C. and additional CPA near −20° C. to −40° C., and can cool and warm organs to and from these temperatures.

11. When an organ is ready to be banked, it can cool the organ to near its glass transition temperature.

12. It is capable of perfusing and cryoprotecting organs of widely varying size, e.g., anything from a rat heart to a human liver, and is capable of tissue superfusion as well.

BRIEF DESCRIPTION OF THE DRAWING

FIG. 2A is a side view. FIG. 2B is a view of the lid of the reservoir as seen from above. FIG. 2C is a view of the reservoir as seen from above without the lid.

DETAILED DESCRIPTION OF THE PREFERRED EMBODIMENTS AND BEST MODE

Figure 1A:
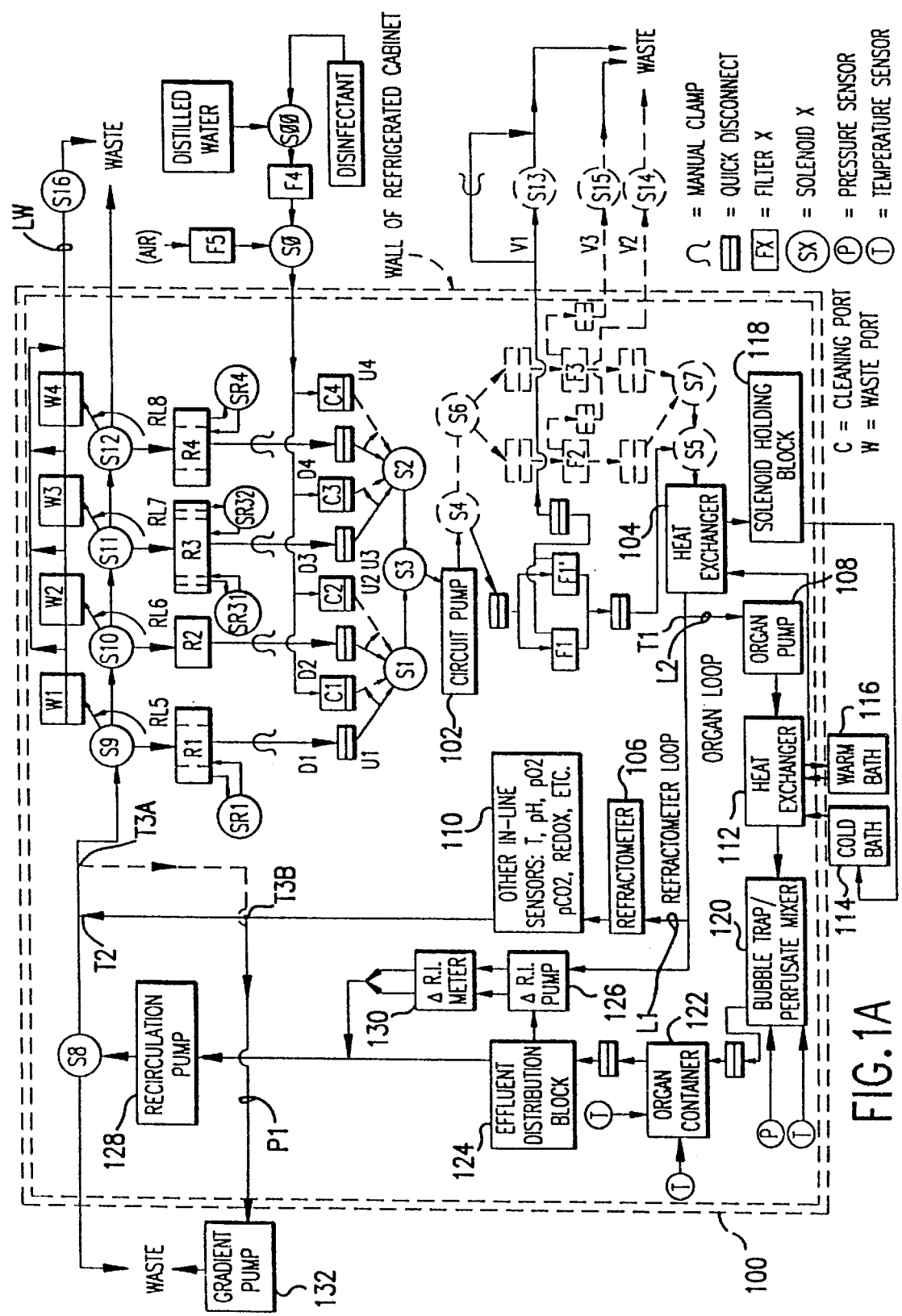
FIG. 1A shows the overall fluidic circuit diagram of one embodiment of an apparatus for carrying out some aspects of this invention.
Figure 1B:
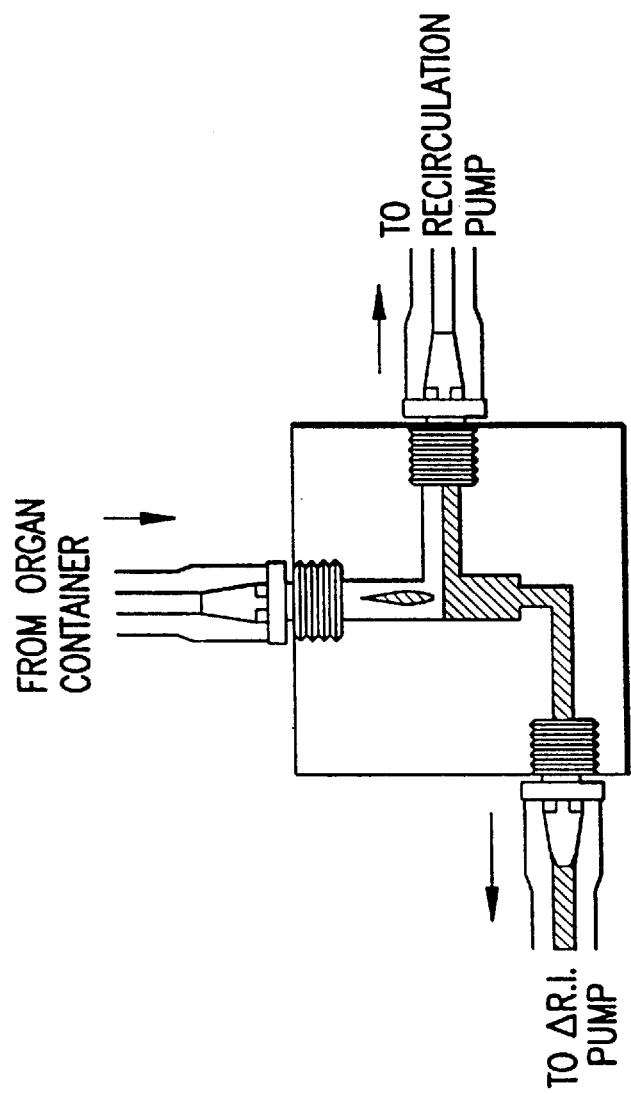
FIG. 1B shows the construction of the Effluent Distribution Block (EDB) and the means by which the effluent flow is divided to allow sampling by the delta R.I. pump 126 in FIG. 1A.

In a first embodiment of this invention, the apparatus is contained in a refrigerated cabinet 100 (shown by double dashed lines in FIG. 1). The refrigerated cabinet contains two sides, the reservoir/solenoid side and the organ/ refractometer side. The cabinet is faced with double paned transparent doors each containing approximately 1 inch of insulating air (which can be reduced in pressure and/or humidity if necessary) between the panes to avoid condensation of moisture on the doors and to minimize heat leak to the cabinet. The organ-side door is split to form a "Dutch door". This allows the upper portion of the organ-side door to be opened and closed to place the organ in the system and to remove the organ without changing the temperature below the upper portion of the door, where the organ container and most other equipment is located. The cabinet may also employ a "Dutch door" on the reservoir side of the cabinet to enable the operator to make any needed adjustments (e.g., fluid addition to the reservoirs, transfer of reservoir upper fluid lines, etc.) without disturbing cabinet temperature to an unnecessary degree.

The primary features of the invention and its mode of operation are shown in the fluidic logic schematic of FIG. 1. All perfusate available for circulation through the system is drawn into the main circuit by a circuit pump 102 through fluid uptake lines U1, U2, U3, or U4 depending upon the computer-controlled actuation pattern of three-way solenoid valves S1, S2, and S3. Uptake lines U1–U4 connect either to fluid delivery lines D1–D4 leading from reservoirs R1–R4, respectively, or to cleaning ports C1–C4, through standard tubing quick disconnects. By clamping D1–D4 and unplugging them from uptake lines U1–U4, lines U1–U4 can be plugged into cleaning ports C1–C4, as indicated by the curved arrows. While this is presently done manually, it will be appreciated by those skilled in the relevant arts that appropriate valves, tubing and controls could be added to handle this task automatically.

In the first embodiment of the invention as constructed, the reservoirs R1–R4 are supported on a thick transparent plastic shelf from which four magnetic stir tables hang which stir the four reservoirs. Thorough stirring of R1, R3, and optionally R4 is necessary for proper generation of the desired concentration-time histories. The on/off states and stir rates of the stir tables are independently controlled.

Ports C1–C4 lead to sources of sterile (distilled) water, air, and disinfectant. Solenoid valves S0 and S00 are interposed in the delivery lines for these sources and are arranged to ensure that traces of disinfectant do not enter the perfusion system by accident. Solenoid S0 controls whether air or fluid will enter the perfusion circuit for cleaning, while solenoid S00 determines whether the fluid selected will be water or disinfectant. The breakup of the main cleaning line into four independent channels outside of the cabinet rather than just before reaching C1–C4 ensures that each channel is independent of the others, i.e., not subject to any meaningful cross-contamination resulting from diffusion of unpurged solution backwards from the fluid uptake lines U1–U4 into the cleaning lines leading to cleaning ports C1–C4.

Distilled water and disinfectant are drawn into the system through a sterilizing filter F4, while air is drawn into the system through an air filter F5. The disinfectant of choice at present is a clinically accepted dialysis machine cold sterilant such as Actril. The cleaning procedure is to wash the perfusate out of the system with water and then to displace the water with sterilant. Prior to the next perfusion, the sterilant is washed out of the system with water and the water is then washed out of the system with air. The system is then primed by displacing the air with appropriate perfusate. The air flush is used to avoid the persistence of any lingering traces of sterilant dissolved in the rinse water, and to avoid any possible dilution of the priming fluid with water (i.e., to reduce the amount of priming fluid needed for displacing water from the system), to allow a visual check of the completeness of priming, and to reduce spillage of water in the cabinet when the reservoirs, filters, and organ cassette are placed into the system after cleaning but before priming. The air purge can, however, be omitted if desired. The air filter is used to prevent contamination from pathogens in the air, if necessary.

Solenoid valves S9–S12 normally direct fluid to reservoirs R1–R4 or to waste. Reservoirs R1–R4 can also be detached from the system by removing recirculation lines RL5–RL8 from reservoirs R1–R4 and plugging them into waste ports W1–W4, respectively (as indicated by curved arrows), allowing reservoirs R1–R4 to be removed from the system for cleaning, sterilizing, and refilling. When reservoirs R1–R4 are removed, valves S9–S12 direct fluid to waste ports W1–W4. The four waste lines corresponding to waste ports W1–W4 converge to a single common waste line LW. A two-way solenoid valve S16 is located on the common waste line. When the waste ports are not in use, the common waste drainage line is blocked by closing valve S16 to prevent any possible backflow of waste or pathogens into the sterile cabinet.

The use of this system of uptake lines U1–U4, which are plugged alternately into reservoir delivery lines D1–D4 or cleaning ports C1–C4, in combination with recirculation lines RL5–RL8, which are plugged alternately into the reservoir internal return lines (not shown in the figure) or into waste ports W1–W4, allows complete sterilization of the perfusion circuit. The blunt ends of the uptake lines U1–U4, delivery lines D1–D4, cleaning ports C1–C4 and waste ports W1–W4 may be sterilized by swabbing with disinfectant when the tubing is being transferred from one alternative position to the other. The tubing transfer is accomplished while applying digital pressure to the tubing so as to occlude it while making the transfer to prevent fluid leaks and further reduce the risk of contamination.

The fluid withdrawn from reservoirs R1–R4 or from ports C1–C4 is delivered through one of several filters F1, F2, and F3, depending upon the state of actuation of solenoid valves S4 through S7. These actuation patterns will be described in more detail below. Experience has shown, however, that a single filter F1 or two filters F1, F1' in parallel will be adequate for most studies (rendering valves S4–S7 optional, as indicated by broken lines) since virtual step changes in concentration can be imposed even when only one filter or two filters in parallel are present in the circuit.

It is desirable to minimize the distance between the circuit pump 102 head and the solenoids S1–S7 to minimize circuit dead space and dead time and minimize the effects of perfusate viscosity.

The filters are capable of sterilizing the perfusate and are autoclavable. All filter holders can be removed from the system for cleaning and sterilization by means of the quick disconnects shown in FIG. 1. Vent lines V1–V3 lead to solenoid valves S13–S15, located outside of the refrigerated portion of the cabinet 100. These vent lines are opened and closed under computer control during priming and cleaning of the system to permit air to escape and thereby prevent the filters from becoming blocked or damaged. A manual bypass (shown only for the S13 bypass) is provided for V1–V3 for emergency purging of air from the circuit. Obviously, air purges of the system beyond filters F1–F3 are not possible if filters F1–F3 are present in the circuit; hence filters F1–F3 must be removed before beginning the washout of sterilant if an air purge is to be included in that procedure.

In the presently preferred embodiment, a 90 mm diameter filter of 0.22 micron pore size is located in each filter holder.

This size filter is able to pass enough vitrification solution at 0° C. to permit the successful perfusion of a rabbit kidney, with an overlying 1.2 micron filter and a coarse prefilter to prevent clogging. The standard configuration for the operative version employs two identical filters in parallel. This is necessary to accommodate the flows required for human organs and provides a safety factor for any air which may be inadvertently introduced into the arterial fluid, as well as minimizing pressure build-up proximal to the filter. This continuous filter sterilization and resterilization of the perfusate during the perfusion can serve as a back up for pre-sterilized solutions in case of contamination for any reason during the perfusion.

Once the fluid from the selected reservoir has passed through the appropriate filter, it goes through some preliminary temperature conditioning in a heat exchanger 104 and then travels to a position as close to the organ as possible, at which point it encounters a "T" type tubing connector T1. The bulk of the flow passively takes the path L1 ("refractometer loop") that leads to a flow-through process control refractometer 106 that measures the index 5 of refraction of the liquid and hence the cryoprotectant concentration. The remainder of the flow is directed through an organ loop L2 by means of an organ pump 108. The organ pump speed is generally controlled by the computer so as to maintain the desired organ perfusion pressure despite wide variations in the organ's vascular resistance. By changing the organ pump head and the diameter of the tubing going through it, a wide range of flows can be generated sufficient to perfuse organs of a wide range of sizes: organs as small as rat hearts and as large as human kidneys have been successfully perfused.

The flow rate delivered by the circuit pump 102, which supplies both the refractometer loop L1 and the organ loop L2, must be high enough to both exceed the flow rate through the organ at all times and to ensure that sufficient flow is available for the refractometer 106 and other in-line sensors, generally designated 110, for measuring temperature, pH, and other desired parameters of the perfusate to permit accurate measurements. The flow must also be high enough to minimize the "dead time" between changes in reservoir concentration and changes in the sensed concentration and other sensed parameters in the refractometer loop as well as to minimize the "dead time" between the reservoir and the organ. The circuit pump flow is limited by the need to prevent fluid from being delivered to the filters at a rate in excess of what these filters or the tubing leading to them can pass without failing, as well as by constraints of heat output and wear and tear on the circuit pump tubing. The speed of the circuit pump is usually not varied during an experiment and does not therefore usually require computer control, though computer control is available as an option.

After passing through the organ pump 108, the perfusate passes through a second heat exchanger 112 that finalizes perfusate temperature conditioning. This is done by adjusting the flow of both cold and warm liquid from cold and warm baths 114, 116, respectively, using computer-controlled pumps (not shown) between heat exchanger 112 and baths 114, 116.

The computer is able to vary flow through both the cold path and the warm path so as to adjust perfusate temperature in the arterial line and therefore also in the effluent of the organ. The arterial and effluent temperatures provide an indication of the actual organ temperature. By controlling the flow rate of cold and warm bath fluid, organ temperature can be adjusted independently of organ flow, provided flow is not close to zero. Experience has shown that arterial and venous temperatures at least as cold as −6° C. and at least as high as 25° C. can be achieved with this invention. Generalized cabinet cooling is not an alternative to the heat exchange system for subzero perfusions because cooling of the cabinets to subzero temperatures will cause freezing of the more dilute solutions in the tubing lines.

The temperature-conditioned perfusate is then debubbled and mixed in a bubble trap/mixer 120 just before entering an organ container 122. Arterial and venous temperature probes, generally designated "T" in FIG. 1, penetrate the wall of organ container 122. Pressure and, optionally, temperature is sensed in the bubble trap. Although shown separately in the drawing for ease of understanding, the bubble trap and mixer 120 are in fact an integral part of the heat exchanger 112, so heat exchange continues to be controlled while debubbling and mixing are accomplished. Experience has shown that mixing is important due to the tendency for layering of dilute solutions on more concentrated, denser solutions. Details as to the specific construction of the heat exchanger/bubble trap/mixer (HBM) are described below.

Under normal circumstances, the cooling fluid effluent from this second heat exchanger 112 is used to cool the perfusate passing through the preliminary heat exchanger 104. This cooling fluid then travels to a solenoid holding block 118 physically containing solenoids S1–S12, so as to draw off waste heat from these solenoids before returning to the cold bath.

The HBM is designed to require removal for cleaning only infrequently. Disinfection and removal of disinfectant from the bubble trap area are effected automatically but presently require some operator attention afterwards to ensure that all uppermost exposed surfaces are disinfected and later washed free of disinfectant without contaminating the outlet tubes. The option exists of arranging the outlet tubes at 413, 416, and 417 in such a way that, with specific solenoids attached to them, they could be individually purged with water, disinfectant, and air under automated control, thus relieving the operator of the need for diligence in cleaning the bubble trap.

After the perfusate exits the HBM unit through port 406, it enters the organ in the organ container 122 (FIG. 1). In the preferred embodiment, the organ container comprises a rectangular box with a hinged lid, lid stop, lid handle, sloped floor, specially sloped feet, arterial and venous thermocouple inlets, perfusate inlet, and effluent outlet in the foot opposite the inlet. The slope of the floor is downward in both the right to left and the back to front directions to ensure that all fluid runs to the foot outlet with very little fluid accumulation anywhere in the container. One needle probe is inserted directly through the wall of the arterial line. A second probe is placed directly in the stream of fluid emerging from the organ. In typical results, the arterial and venous temperatures differ by only tenths of a degree, but both are useful for quality control. The organ container may employ a soft mesh support for the organ similar to that used in the MOX-100 DCM™ organ cassette (Waters Instruments Inc., Rochester, Minn.) or the organ can be placed directly on the floor of the organ container or on a specially designed independent and removable support. The latter option is preferred and is presently in use.

The holding block 118 currently consists of a large aluminum block (but may be either metal or plastic) perforated with cylindrical holes of sufficient diameter to closely match the outside diameters of the held solenoids. The solenoids are inserted such that the base, containing the fluid inlets and outlets, faces the operator and the head, from which the electrical leads originate penetrates into or through the holding block. The solenoid holding block is equipped with an internal fluid path for drawing off waste heat from the solenoids. Feet are provided to position the holding block, prevent it from moving, and protect the fluid inlet and outlet ports when the holding block is removed from the cabinet. The block is positioned behind and above the reservoirs in the refrigerated cabinet so that the solenoid inlets and outlets and their connections to the reservoirs are always readily visible.

The solenoids are preferably 3–7 watt (or less) piston type 3-way solenoids of minimal internal fluid volume having orifices on the order of 0.156 inches or more and Cv values >0.16 or more (e.g., NR (Neptune Research) Model 648T033 fitted with RC dropping circuits and 3-watt coils) while resisting pressures of up to 500 mmHg or so. Solenoids having $\frac{1}{16}$ inch orifices and Cv values of 0.01 to 0.03 (e.g., Valcor's Model 20-2-3) are not fully satisfactory due to the high viscosity of the solutions used for cryopreservation (causing difficulty aspirating viscous fluid through S1–S3), the high flows desired for controlling dead times and for perfusing larger organs, the possibility of clogging, and the buildup of pressure between the circuit pump and S8–S12. The detailed actuation pattern and tubing arrangement of the solenoids is described below. The internal solenoids not held in the solenoid block, SR1, SR31 and SR32, are described in more detail below.

An effluent distribution block (EDB) 124 (FIG. 1) is connected to the output side of the organ container 122. The EDB is designed so that a small amount of effluent is always present at the bottom of the block. This effluent or residual fluid is withdrawn by the two-channel "delta R.I. pump" 126 and sent to the differential refractometer ("delta R.I. meter") 130 where its refractive index is compared to that of the arterial perfusate from refractometer loop L1 (pumped at the same rate as the venous effluent sample) and a difference signal generated. EDB 124 is drained also by the effluent recirculation pump 128. The EDB 124 therefore allows effluent to be recirculated with or without first being delivered by the delta R.I. pump 126 to a differential refractometer 130. The differential refractometer 130 sends a signal to the computer which provides a measurement of the difference in concentration between the fluid in the refractometer loop L1 and the organ effluent in the organ loop L2. The nonlinear baseline resulting from this unorthodox use of the differential refractometer is accounted for in the software for running the perfusion program. Since the fluid in the refractometer loop will approximate the concentration of the fluid entering the artery of the organ, the delta R.I. output provides an estimate of the arteriovenous concentration gradient across the organ. When this gradient is large (in either the positive or negative direction), the organ is far from equilibrium. When the gradient is zero, the organ is at least largely in osmotic equilibrium with the perfusate.

All effluent from the organ (together with the arterial fluid sampled by the delta R.I. pump) is ultimately collected by the recirculation pump 128 and sent to solenoid S8, which controls whether the effluent is recirculated to the reservoirs or discarded to waste. Effluent to be returned to a reservoir is combined with the fluid flowing through the refractometer loop L1 at a T connection T2. As noted above, return to the correct reservoir is then controlled by the actuation of solenoids S9 through S12.

The recirculation pump 128, like the circuit pump 102, need not require flow adjustment. It is normally set to a rate sufficient to exceed the maximum steady flow through the organ pump 108. Since the output of the recirculation pump exceeds that of the organ pump, air is continually introduced into the tubing leading to solenoid S8 and usually to the reservoirs R1–R4. Provisions to prevent excessive bubbling of the reservoirs as a result of this are described below.

Although the delta R.I. pump speed can be changed, it is usually kept constant throughout an experiment. In the presently operative version, it is not under computer control, but computer control would be a desirable option in some cases. The delta R.I. pump employs very small diameter tubing to reduce delays in fluid transit time. This small tubing is particularly important because the flow rate through the delta R.I. circuit is limited by the lowest flow rate through the organ, which may be small, and by the limited size of the fluid paths in commercially available differential refractometers.

The return of the differential refractometer output to the organ effluent line is proximal to the effluent recirculation pump. This placement rather than placement distal to the pump ensures a steady flow though the differential refractometer, whereas distal placement may prevent or alter differential refractometer flow by virtue of a higher exit pressure.

The present operative version of the embodiment of the invention uses silastic tubing of $\frac{1}{8}$ inch diameter throughout the system, which is sufficient to accommodate the needed flows and is preferred. Silastic is compatible with Actril cold sterilant, is translucent (important for visualizing flow to detect problems and for observing any signs of microbial growth), is impervious to common cryoprotective agents such as dimethyl sulfoxide, and is soft enough to be easily manipulated. However, silastic should not be used in circuits coming into contact with silicone cooling fluids, which swell and weaken silastic tubing.

Figure 2A:
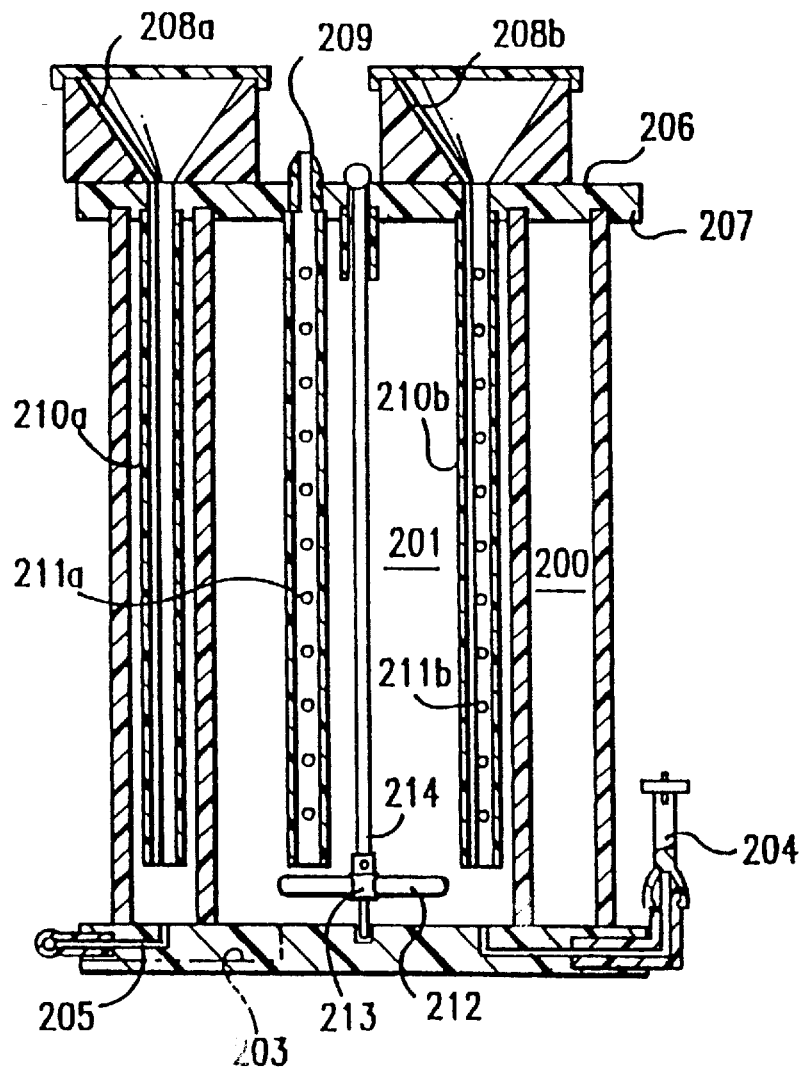
FIGS. 2A–C show views, of a two-chamber gradient former employed as reservoir R1 in this invention.
Figure 2B:
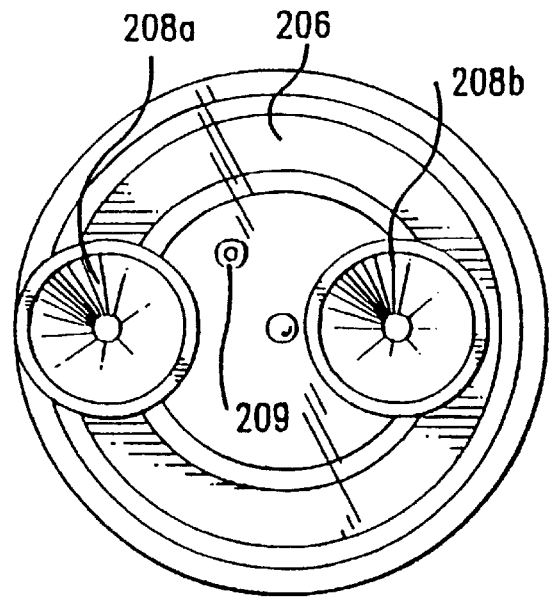
Figure 2C:
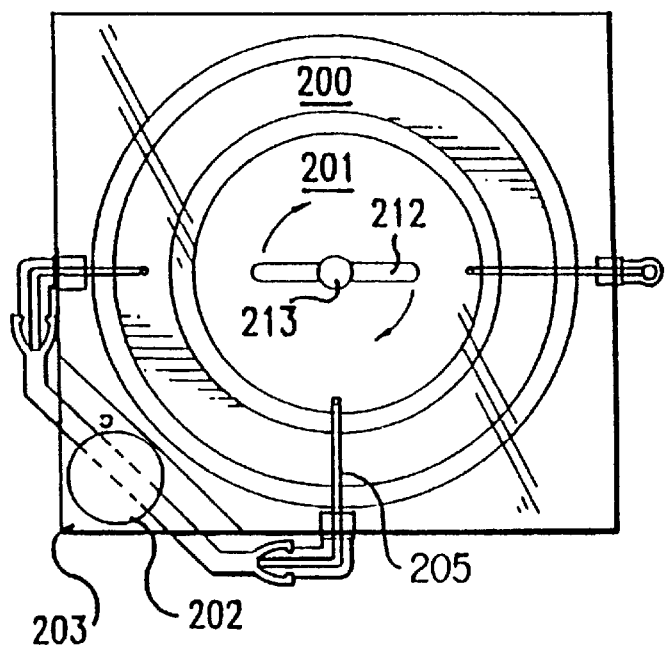

Reservoir R1 is constructed as a gradient former (FIG. 2). Essentially the gradient former consists of two concentric cylinders, an outer cylinder 200 and an inner cylinder 201. A fluid path 205 allows fluid to flow from the outer cylinder 200 to the inner cylinder 201 under the influence of gravity in response to a reduction of volume in the inner cylinder. The concentric orientation of the fluid compartments is very space efficient. The fluid delivery line 204 corresponds to the line D1 of FIG. 1. The unit shown is a modification of a commercially available gradient former. The necessary modifications for use with this invention are as follows.

1) The stopcock normally used to control flow from the outer cylinder to the inner cylinder in the commercial device is replaced by a pinchtype two-way (on/off) solenoid valve 202 (currently, a Bio-Chem Valve Corp. model 100P2WNC). The pinch-type valve is preferable for this application to a piston-type valve because of the small pressure difference available to drive fluid flow and the consequent need for a large working diameter fluid path. It is also preferable for easy removal from its tubing when the reservoir is to be removed from the cabinet for cleaning, leaving the solenoid behind. The base of the gradient former has been modified, at 203, to make room for the solenoid and to support it on a platform so as to keep the solenoid oriented correctly. The solenoid is located a sufficient distance from the reservoir to avoid excessive heating of the reservoir fluids.

2) The diameter of the fluid path 205 from the outer cylinder 200 to the inner cylinder 201 has been enlarged to permit flow at an adequate rate of the viscous solutions required for organ cryopreservation. An inner diameter of $\frac{1}{8}$ to $\frac{3}{16}$ inch is adequate.

3) A lid 206 has been provided. The lid has an outer overhang 207 that prevents the lid from moving from side to side after it is placed on the cylinder. The lid has built-in outer and inner filling funnels 208a and 208b and a recirculation port 209.

4) Funnels 208a and 208b extend into respective internal fill tubes 210a and 210b. The internal fill tubes are preferably rigid hollow rods located next to the wall of the inner and outer cylinders and perforated at 1–2 cm intervals with holes 211a and 211b, respectively, which are approximately 3 mm in diameter. The function of the fill tubes is to reduce the creation of bubbles as recirculating fluid impacts the surface of the liquid in the reservoir. The purpose of the perforations is to enable air to escape from the tube through the perforations so as not to force air to the bottom of the reservoir to form bubbles. These functions are particularly important in perfusates containing protein, which tend to stabilize bubbles.

5) A fill mark has been provided to enable the reservoir to be filled reproducibly to the same, predetermined volume. The operator can establish his/her own fill mark depending upon the details of the application. The gradient formers have approximate graduations (horizontal lines on both the inner and outer cylinders, aligned so as to permit avoidance of parallax error in reading the liquid level in either cylinder) spaced approximately 0.5 cm apart for a 2 liter gradient former. These graduations are also important for establishing slight, deliberate mismatches in liquid level between inner and outer cylinders, which are necessary to prevent premature mixing of solutions of widely differing densities, such as cryoprotectant-free perfusate and vitrification solution. They also permit a rough quantitative check by the operator on the progress of the gradient as represented on the computer screen.

6) The plastic composition of commercially available gradient formers may create problems for certain types of cryoprotectant, which could conceivably attack the plastic. It is therefore preferred to use reservoirs made of transparent material (e.g., glass, plexiglass or the like) that is compatible with the cryoprotectant chemicals or use reservoirs whose surfaces have been siliconized or otherwise treated to prevent the attack. In the inventor's experience, acrylic has been found to be an acceptable material.

7) The reservoir R1 contains a stir bar 212. The stir bar is housed in a jacket 213 attached to a freely spinning vertical pin 214 extending to the stir bar from the lid of the reservoir to prevent the jacket, and hence the stir bar, from moving laterally. This change is necessary to make sure chattering, and therefore poor mixing, does not occur while the perfusion machine is unattended. Support from above rather than below prevents unnecessary perfusate frictional heating and avoids drainage/cleaning problems.

Figure 3A:
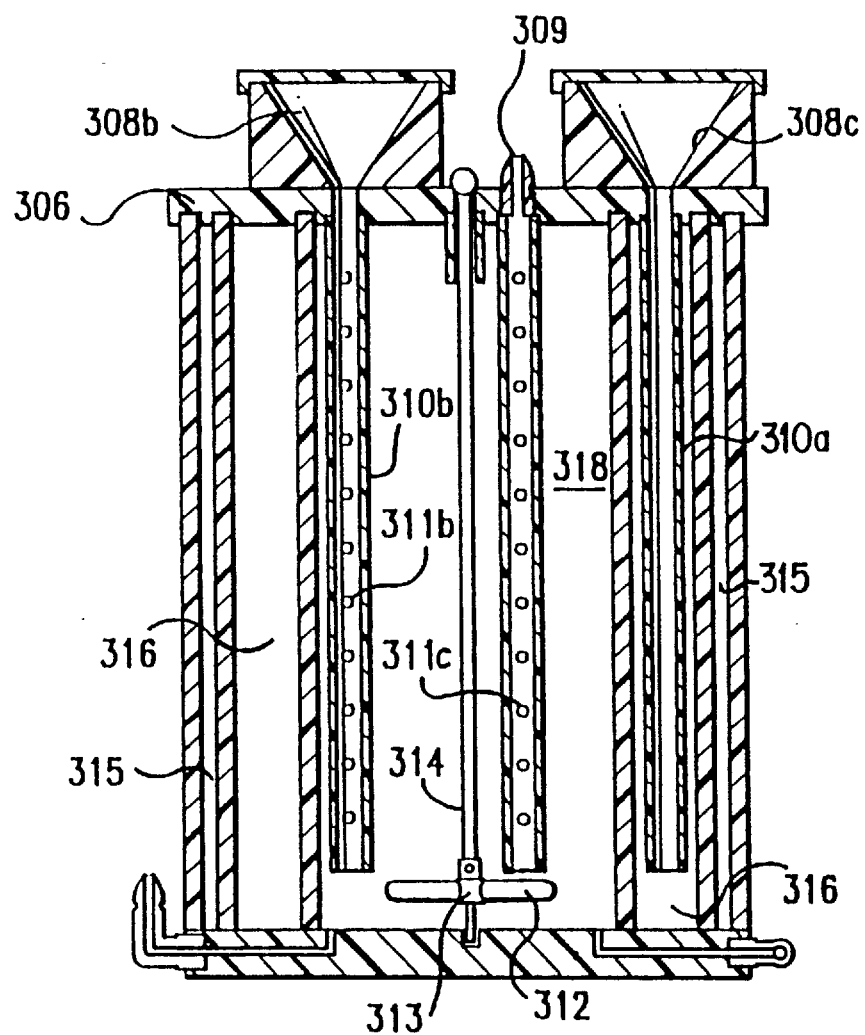
FIGS. 3A–C show side, top and bottom views, respectively, of a three-chamber gradient former used as reservoir R3 in this invention.
Figure 3B:
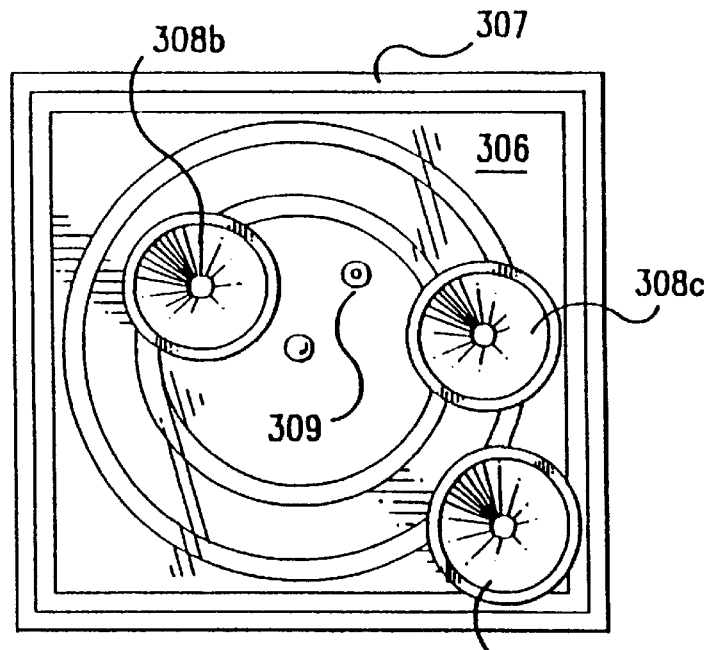
Figure 3C:
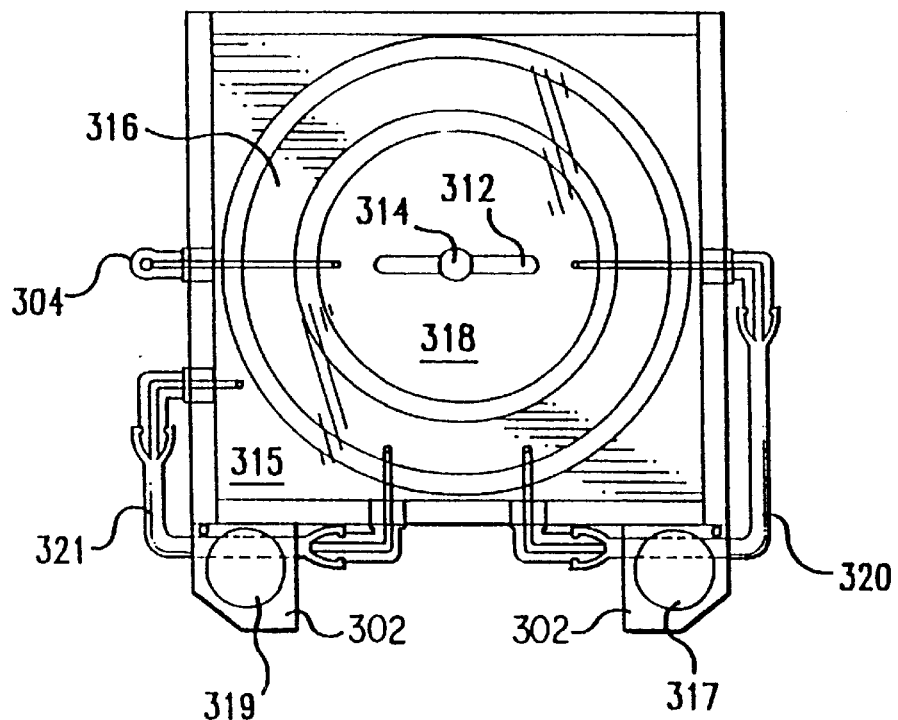

Reservoir R3 is also constructed as a gradient former. The details of reservoir R3 are shown in FIG. 3. In the drawing, those elements that are substantially the same as in reservoir R1 are designated with the same reference number, except that the first digit has been changed from a "2" to a "3". Reservoir R3 contains an outer compartment 315 ($R3_3$), an inner compartment 318 ($R3_1$), and a third intermediate compartment 316 ($R3_2$). Intermediate compartment 316 is connected to inner compartment 318 through a fluid conduit 320 controlled by a solenoid 317 ($SR3_1$). Compartment 316 also connects to outer compartment 315 by a fluid conduit 321 controlled by a solenoid 319 ($SR3_2$). The use of an outer compartment is necessary when concentration is being reduced to zero or nearly zero, for reasons noted below in the discussion of the function of the gradient pump and the action of the gradient formers. The outer compartment is necessary in preference to a larger volume of fluid in the middle compartment because increasing the volume of fluid in the middle compartment will cause the concentration profile of fluid flowing from the gradient former to waste in response to a constant efflux rate of inner cylinder fluid to become non-linear, therefore making control of concentration-time history more complicated. More importantly, an excessive amount of fluid in the middle compartment would be required to approach a zero concentration in the circuit compared to the amount of fluid required in the outer compartment after virtual emptying of the inner and middle compartments.

Automated use of reservoir R3 poses some problems which are successfully addressed in part by software and in part by the specific construction of R3. Specifically, actuation of solenoid $SR3_2$ allows fluid in the outer compartment ($R3_3$) to flow first into the middle compartment ($R3_2$) and from this compartment to the inner cylinder ($R3_1$). This is because the pressure head present between $R3_3$ and $R3_2$ is large when $R3_1$ and $R3_2$ are nearly empty, which occurs when $SR3_2$ is activated. At this point, $R3_3$ is still full. This large pressure head causes fluid to flow too rapidly into $R3_1$ if $R3_3$ is connected directly to $R3_1$ rather than using $R3_2$ as a buffer between $R3_3$ and $R3_1$. By adjusting the level of $R3_3$, the flow can also be partially controlled. But even with these two precautions, further control of flow is required by using an appropriate duty cycle for $SR3_2$. The flow to $R3_1$ should be slow at first and more and more rapid as the concentration is brought closer and closer to zero, whereas passive flow under the influence of gravity will always be fastest at first and slowest at the end unless the flow is metered by the sort of tailored duty cycle currently being imposed on $SR3_2$.

The other modifications to R3 resemble those of R1.

Reservoir R4 is a gradient former constructed in the same manner as R1.

An important element of the fluidic circuit is the gradient pump 132 connected to the circuit by a line P1 (FIG. 1). The function of the gradient pump is to allow for gradual changes in concentration within the appropriate reservoirs within the cabinet. The method by which this is accomplished will be described below. The placement of the line P1 to the gradient pump at T3A, just after the point of joining of the refractometer loop L1 and the organ loop L2, presents one option for ensures removal of some of the air introduced by the organ effluent recirculation pump 128 and therefore helps reduce bubbling of the reservoir fluid.

A better option, however, and the one presently in use, is to draw no air into line P1. This is accomplished by connecting P1 at point T3B and results in fully controlled concentration-time histories. The bubbling problem is then overcome by continuously regulating the speed of the recirculation pump 128 to be just slightly in excess of the combined flows of the organ pump 108 and the delta R.I. pump 126 so as to introduce little air. Attaching the recirculation output of S8 directly to P1 without regulating the speed of pump 128 results in degraded concentration history and is not recommended.

The purpose of the gradient pump 132 is to remove some of the recirculating fluid from the circuit. This removal of fluid causes the flow rate of fluid back to the reservoir of origin to be less than the flow rate of fluid from this reservoir to the circuit. This causes the level in the inner cylinder of the reservoir (R1, R3, or R4) to go down. This lowering of inner cylinder fluid level in turn causes the fluid in the outer or middle compartments to flow into the inner cylinder to keep the two levels similar. Thus the two dissimilar concentrations in the two cylinders are mixed in the inner cylinder, generating the concentration gradient which is then sent to the rest of the circuit. This is the manner in which the gradient pump effects the desired gradual changes in concentration which reach the organ and the refractometers. Any necessary adjustments to the gradient pump speed are made by the computer.

The principle involved is that of an ordinary linear gradient former in which the portion of the circuit external to the gradient former can be regarded, to a first approximation, as extra volume in the inner cylinder. Withdrawal and discard of fluid from the inner cylinder at a constant rate will result in a linear molar concentration increase with time despite the presence of the rest of the circuit and the recirculation of fluid back to the reservoir. However, unlike an ordinary gradient former, the concentration of fluid leaving the gradient former at the moment the volume in the gradient former becomes zero will not be equal to the concentration of fluid in the outer (or middle) cylinder of the gradient former. Therefore, in order to approach a concentration of zero during cryoprotectant washout using an ordinary two-compartment gradient former, it is necessary to add additional fluid to the outer cylinder while continuing to discard fluid from the inner cylinder normally. This is why R3 has been modified to have a third compartment: the extra fluid required to continue cryoprotectant washout can be added from this third compartment by the computer without operator intervention which could compromise temperature control and introduce inaccuracies. During introduction of cryoprotectant, on the other hand, the desired final concentration can always be reached by using a concentration in the outer compartment which significantly exceeds the final concentration desired in the circuit at the end of the gradient.

The HBM heat exchange system is shown in detail in FIGS. 4A–E.

Perfusate enters the HBM through an entry port 403, travels through a central channel 400, and leaves the HBM via an outlet port 406. On either side of the central perfusate path are separate chambers for regulating temperature. The two innermost temperature control chambers 401 (one on each side of the perfusate path) are used for the circulation of coolant, while the outer chambers 402 are a pathway for the flow of room temperature fluid for offsetting the coolant. (For specialized applications involving, for example, normothermic perfusion, these pathways can be reversed.)

The direction of cold fluid flow is optional. Adequate temperature control has been found when all fluids (perfusate, coolant, and warming fluid) flow in the same direction (uphill) despite the lack of countercurrent heat exchange. This mode allows the avoidance of air or carbon dioxide accumulation in the outer chambers.

Perfusate enters the bottom of the HBM unit through inlet 403 and travels upward in a zig zag pattern. It emerges into a small upper reservoir which has an air space above: this is the bubble trap area 404. Perfusate then travels beneath the bubble trap and goes through a perfusate mixing area 405 before finally traveling onward to the arterial outlet.

The inlets for cold 407 and warm 408 fluid are each split into two channels within the base of the unit. The outlets 410, 411 for warm and cold fluid, respectively, each receive fluid collected from two channels such that each channel of the same kind (i.e., each cold channel or each warm channel) is the same length and nominally experiences the same pressure difference from start to finish, so that flow rate through each like channel should be approximately equal.

All of the cold and warm fluid pathways include a length of flexible tubing 412 at the rear of the unit. These tubing segments serve two purposes. First, by introducing an air gap between the four channels, heat exchange between them is minimized. This is particularly desirable when all of the cold and warm fluid is flowing in the direction opposite to that of perfusate flow (i.e., in orthograde direction) and has not already undergone heat exchange with the perfusate. Second, each tube can be clamped. In this way, if by chance one cold channel or one warm channel should take all of the cold or warm fluid delivered while the other channel "airlocks", this situation can be corrected by clamping the channel receiving all of the flow and purging the air out of the inactive channel, bringing each channel into full function and equal flow.

Because in orthograde mode the temperature conditioning fluid enters the heat exchanging portion of the unit at the top and exits at the bottom, it is necessary upon installation to run the cold and hot pumps in retrograde direction in order to purge all air out of the cold and warm channels. This is best accomplished if the cold and warm tubing leading to and from the bath is no more than about ⅛ inch in internal diameter, since at this diameter fluid flow will displace air from the tubing rather than allowing it to flow uphill in a direction opposite to the direction of fluid flow or otherwise to remain unpurged in various parts of the tubing. Thus, when the pump direction is reversed again from retrograde to orthograde, no air will be present in the tubing and none will be trapped in the heat exchange chambers of the unit.

In addition to serving a heat exchange function, the zig zag pattern is also designed to force mixing of previously perfused dense perfusate or, when perfusate density is rising rather than falling, to purge the less dense perfusate from the perfusate path.

As the perfusate emerges from the zig zag heat exchange area, it enters the bubble trap 404 at trap entry area 418. Perfusate exits the bubble trap through exit region 419. The zig zag pattern, in fact, is also designed to allow any air bubbles to exit the heat exchange area and to emerge into the bubble trap area. The bubble trap area is designed to have the following features.

1. Its volume is sufficiently large to reduce the pulsatile action of the perfusion pump to a minimum by distributing the shock of each stroke over a relatively large air volume. This simplifies pressure control and measurement and may be less damaging to the organ.

2. Its volume is sufficiently low to minimize the liquid volume present in the trap and thereby to minimize the dead time and dead volume between the organ pump and the organ itself. A minimal volume is also desirable to minimize layering of more dilute perfusate over more dense perfusate.

3. A pressure sensing port 413 is provided. Port 413 has no fluid connection to the perfusate, thus eliminating a "blind alley" in which fluid cannot be mixed properly or in which disinfectant might fail to penetrate or might be trapped.

4. The lid 414 of the trap is removable for cleaning.

5. A vent port 416 may be provided which is used to adjust fluid level in the trap so as to make it the minimum required to serve the bubble trap function and to maximize pressure wave damping. The tubing from this vent leads to the outside of the cabinet, permitting adjustments to be made without opening the cabinet door. The same port leads to the electronic pressure transducer as well.

6. A third port 417 is provided through the bubble trap lid to permit the injection of drugs, vascular labeling materials, fixative, etc.

7. The walls of the bubble trap are angled near the trap entry and exit points 418, 419, respectively, to produce a certain amount of mixing of the perfusate both as it enters and as it leaves the trap, and to break up and minimize the volume of layers of dilute perfusate overlying more dense perfusate.

8. The option exists of introducing probes, such as a temperature probe via one of the ports in the trap lid to make measurements in the perfusate without permanent embedding of the sensor: the port consists of flexible tubing attached to a plastic threaded fitting. A probe can be freely admitted or withdrawn and the tubing clamped with hemostats or an equivalent clamp to effect a pressure-tight seal. This simplifies removal and reinstallation of the HBM when it must be cleaned and allows flexibility in probe selection and the opportunity of using the probe for other measurements elsewhere.

Figure 4A:
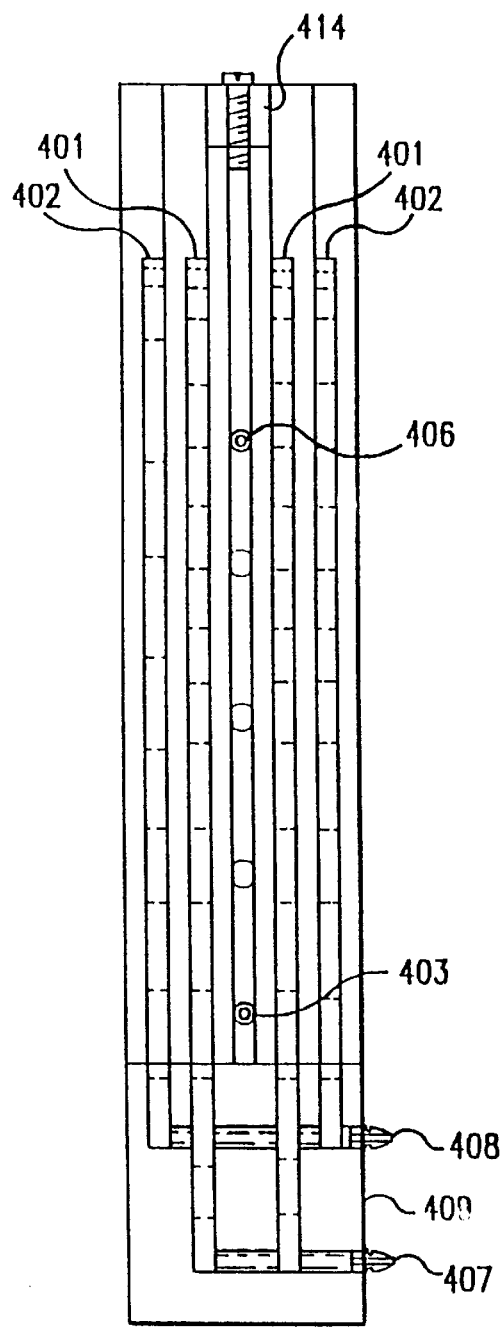
FIGS. 4A–C show front, side and rear views, respectively, of the heat exchanger/bubble trap/mixer (HBM) used in this invention.
Figure 4B:
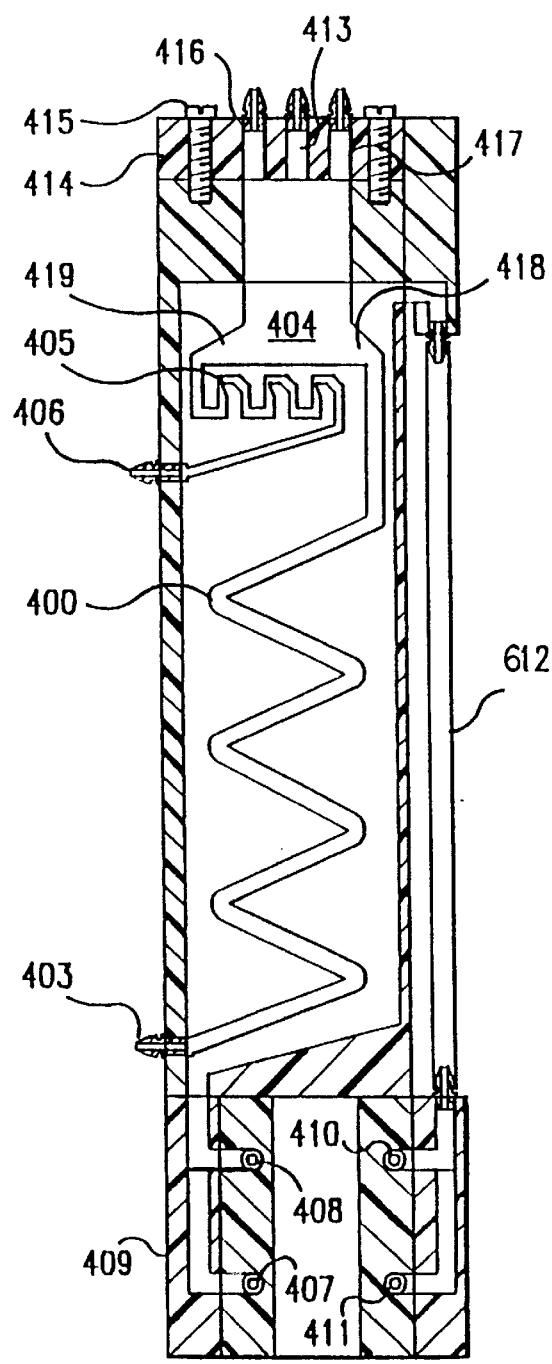
Figure 4C:
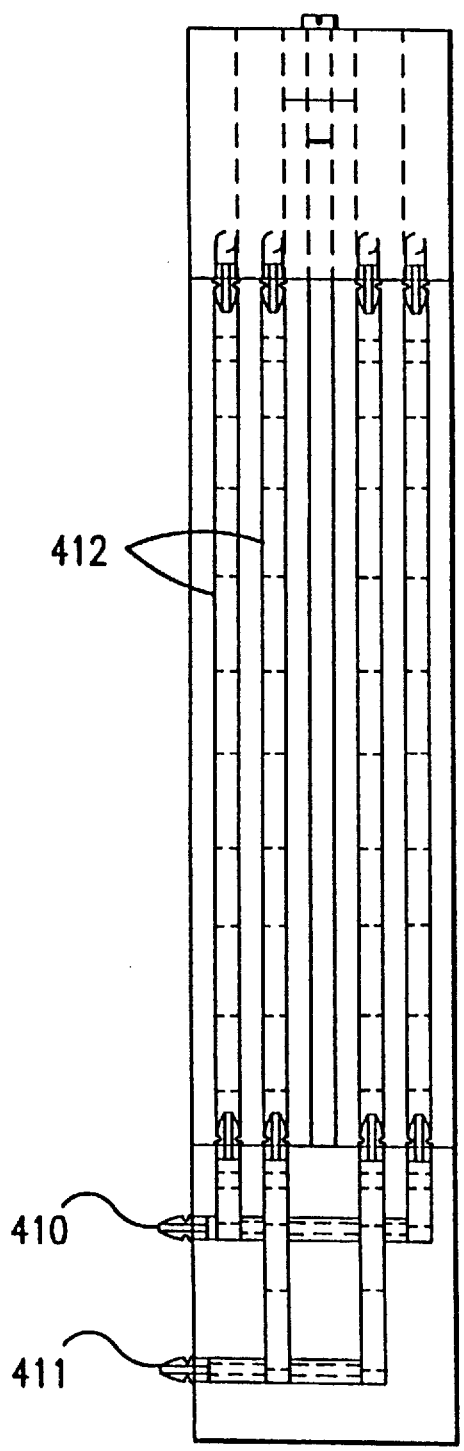
Figure 4D:
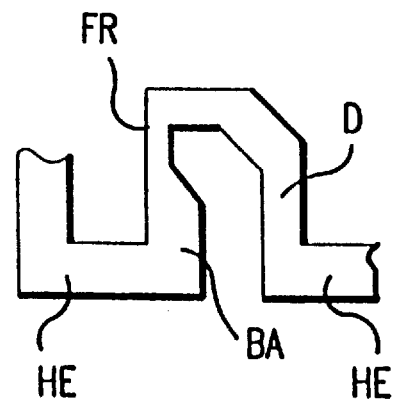
FIG. 4D shows the basic mixing area of the HBM.
Figure 4E:
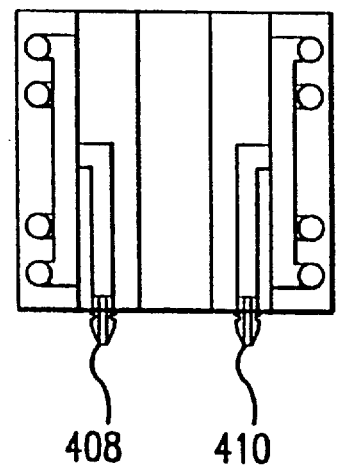
FIG. 4E shows a top view of the base of the HBM.

After leaving the bubble trap, the perfusate descends to a mixing area 405 (see FIG. 4D). The basic unit of the 3-unit mixing path is a narrow horizontal entry area HE emerging into a "wide" basal area BA which rises to an area of flow restriction FR and ends in a descent D to the next horizontal entry area. Fluid entering HE is forced through an opening too small to support much layering of low density fluid on top of high density fluid, especially considering the right angle turn required just before HE. Fluid flowing into BA may, if less dense, rise immediately upward toward FR. If more dense, it may be driven into the wall W and rise upward along this wall. Upon encountering FR, however, the denser liquid will be accelerated toward the less dense liquid rising directly from HE, creating turbulence and mixing. If BA fills with dense perfusate, the speed of the fluid emerging at FR directly upwards toward D should cause the dense liquid to mix with any low density fluid layered above FR. Furthermore, the narrow descending path D should draw layered liquid down the angle along with denser liquid, again preventing stagnant layers from persisting. In practice, three such mixing units aligned in series as shown in FIG. 4B are sufficient to mix initially very poorly mixed perfusate, which is encountered frequently in the course of abruptly raising or lowering cryoprotectant concentration. One final function of the mixing units is to serve as a trap for any small bubbles which for any reason are not removed in the bubble trap area. (Bubbles in the mixing area are, however, easily purged by the operator prior to initiation of organ perfusion.)

After leaving the mixing region, the perfusate descends to an outlet port 406 leading directly to the organ. The path from the final mixing unit to port 406 is deliberately created at an angle to the horizontal in order to provide one last chance of stopping any bubbles from reaching the organ, since in order to reach the organ a bubble in this pathway would have to flow downhill, contrary to its tendency to flow uphill.

The mixing area and subsequent areas are purged of air by occluding the outlet tubing affixed to port 406 with the vent open until approximately ½ inch of fluid has accumulated in the bubble trap. The vent is then closed until the pressure has reached about 60–120 mmHg. Finally fluid is once again allowed to flow freely through port 406. The jet of fluid through the mixing area and out port 406 sweeps all air out of the fluid path from the bubble trap to port 406. If some air persists, it can be removed by repeating the process. After air has been purged, the vent is opened to allow unnecessary fluid in the bubble trap to exit the trap under the influence of gravity, reaching a final depth of about ⅛ inch. A final depth of ⅛ inch cannot be set before purging the line of air because insufficient volume exists to avoid refilling the mixing area with air from the bubble trap during the purging process.

The organ container 122 and the organ pump 108 are placed in maximum proximity to reduce dead times and dead volumes between the two, and the tubing leading from the organ pump to the organ container is chosen to be as small in inner diameter as possible for the same reason.

Most perfusate does not go through the organ loop L2 as described above but travels instead from the filters to the in-line analogue refractometer 106. The presently preferred embodiment of the invention uses a modified commercially available refractometer from Anacon corporation. In particular, small diameter tubing inlet and outlets are used rather than the very large standard Anacon pipe fittings.

The modification of the refractometer sensing head appropriate for the final invention could contain the following changes from the ordinarily available Anacon unit.

1. The internal volume of the fluid path could be kept to a minimum.

2. Presently, it is necessary to purge the air space of the unit with a slow flow of dry nitrogen gas to prevent condensation of moisture due to the low temperatures and high humidities prevailing in the cabinet. In a modified version, the electronics area of the sensing device could be hermetically sealed with some desiccant inside to eliminate the need for a nitrogen purge.

The invention allows the operator to access reservoirs in any sequence and to otherwise custom-design the process which may be of interest. The operator is even free to switch solenoid positions depending on what he may want to do. Nevertheless, the following nominal application illustrates the actuation patterns required to deliver fluid from and to each individual reservoir and filter. It also illustrates the "standard protocols" for organ cryoprotectant perfusion and for cleaning of the system which the system was designed primarily to carry out.

Solenoid S1 admits fluid from R1 when off, or from R2 when activated. Solenoid S2 is open to R3 when not energized, or to R4 when energized. The output of S1 and S2 is to S3, which accepts fluid from S1 (that is, from R1 or R2) when in the resting state and which accepts fluid from S2 (i.e., from R3 or R4) when activated. The common outlet for S3 (always open) leads to the circuit pump 102, which then withdraws fluid from the solenoid-selected reservoir.

If differential filters are to be included, then the output of the circuit pump 102 is to S4's common port (always open). When S4 is not energized, its output is directed to filter F1. The return from filter F1 returns to the normally open port of S5 and exits through the S5 common outlet to the refractometer loop L1 and the organ loop L2. If, on the other hand, S4 is energized, then its output is directed to the common inlet port of S6. When S6 is in the resting state, its output is directed to filter F2, and the return from filter F2 enters S7 through its normally open port. The output from S7 travels to the normally closed port of S5, which must be energized to accept this output. Once fluid has entered S5, it flows out the S5 common outlet to the refractometer loop and the organ loop. Finally if S4 is energized and S6 is also energized, fluid will be directed through both of these valves and will reach filter F3. The return from filter F3 occurs via the energized S7 and the energized S5 solenoids and goes to the two loops L1 and L2 as above. As noted earlier, the use of filters F2 and F3 and therefore of solenoids S4, S5, S6, and S7 is optional and will be useful primarily when very abrupt changes from one solution to another are required, or when particularly heavy particulate contaminates must be removed.

Effluent from the organ eventually returns to S8. If S8 is activated, the fluid is discarded. If S8 is not activated, the fluid is directed from S8 to combine with fluid from the refractometer loop and returned to a desired reservoir.

Fluid traveling through the refractometer loop travels successively to solenoids S9 S10, S11, and S12 and then to waste if none of these solenoids are energized. Energizing S9 diverts flow to the R1 recirculation line. S10's activation (in the absence of activation of S9) diverts flow to R2. Similarly, selective activation of S11 or S12 will, respectively, recirculate fluid to R3 or R4.

There are two basic processes of solenoid-actuated fluid control, one for actual perfusions and one for system cleaning and priming. The perfusion process typically proceeds from R1 through R4 whereas priming must occur in the reverse order to load the fluid uptake and fluid recirculation lines for reservoirs R2–R4 and, optionally filters F2 and F3 and their associated lines) while leaving the circuit primed with fluid from (typically) R1 (or C1) at the end of the priming (or cleaning) process. The typical sequence of solenoid activations required to prime the system (or to clean it) is as follows.

When only F1 (not F2) is present, priming (and cleaning) may proceed in any order of reservoirs, provided, in the case of priming, that the final reservoir corresponds to the first reservoir used for the subsequent perfusion.

Solenoid Control Sequence For Standardized Rinsing/Priming

The conditions of the solenoid control processes are set forth in Tables 1 and 2. The uses of these control processes are to: replace perfusate with filter-sterilized $H_2O$ at the end of the process; replace cleaning $H_2O$ with chemical sterilant between perfusions; remove disinfectant using filter-sterilized distilled $H_2O$; remove water using air; remove air using reservoir fluid, i.e. prime the system.

When only F1 (not F2 or F3) is present, priming (and cleaning) may proceed in any order of reservoirs, provided, in the case of priming, that the final reservoir corresponds to the first reservoir used for the subsequent perfusion. Applicants now use a procedure involving momentary aspiration from R2, then $R3_1$ then R4, then R1, taking just enough time to prime U2, U3, U4, and U1, respectively, followed by computer/user interactive activation of S12, S11, S10, and S9 to allow manual filling of RL8, RL7, RL6, and RL5 by syringe with retrograde exhaust via P1, because this procedure saves large quantities of perfusate and is fast.

The standard process of solenoid actuation for withdrawing fluid from R1–R4 and for creating gradients for a normal perfusion is as follows (assuming (1) use of optional filters F2 and F3, (2) straightforward or typical use of the gradient-controlling solenoids, and (3) the existence of a gradient former as R2). The staged completion of a closed circuit upon going from one reservoir to another is to avoid recirculating solution of undesired composition to the new reservoir before its contents have displaced the previous solution from the circuit. If there is no problem with recirculating the previous solution, the precaution of delayed recirculation can be dropped.

TABLE 1

| Sub-Task Accomplished | Solenoid # (+ = Energized) | | | | | | | | | | | | | |
|---|---|---|---|---|---|---|---|---|---|---|---|---|---|---|
| | 00*0* | 1 | 2 | 3 | 4 | 5 | 6 | 7 | 8 | 9 | 10 | 11 | 12 | 13 |
| 1. Deliver fluid from R4 through F1 | − | + | + | − | − | − | − | − | − | − | − | − | − | ** |
| 2. Perfuse R4 recirculation tubing to W4 | − | + | + | − | − | − | − | − | − | − | − | − | + | − |
| 3. Deliver from R3 through F3 | − | − | + | + | + | + | + | − | − | − | − | − | − | ** |
| 4. Perfuse R3 recirculation tubing to W3 | − | − | + | + | + | + | + | − | − | − | + | − | − | − |
| 5. R2, F2 | + | − | − | + | + | − | − | − | − | − | − | − | − | ** |
| 6. R2 recirculation tubing to W2 | + | − | − | + | + | − | − | − | − | + | − | − | − | − |
| 7. R1, F1 | − | − | − | − | − | − | − | − | − | − | − | − | − | ** |
| 8. R1 recirculation tubing to W1 | − | − | − | − | − | − | − | − | + | − | − | − | − | − |
| 9. Organ loop discard tubing*** | − | − | − | − | − | − | − | + | + | − | − | − | − | − |

*If the sequence above is to be done with reservoir fluid, S0 and SS00 will be off: S0 and S00 will also be off if the sequence above is to be done with water, and the cleaning ports C1–C4 will be connected to uptake line's U1–U4. If the sequence above is to be done with disinfectant, S0 will be off and S00 will be on. If the sequence is to be done with air, S0 will be on and S00 will be off.
S13 (and, optionally, S14 and S15), the filter vent solenoid(s), will be on for a portion of this step and off for the remainder of this step: it will be on just long enough to purge air from the line (usually 60 sec. on step 1 and 30 sec on each of the remaining steps for which the notation is used). This can be programmed not to happen if the filters are not present in the system.
***this step is omitted when priming the system.
Note: Water control solenoid S16 is on (Waste tube open for disposal of fluid to waste) for steps 2, 4, 6, 8, and 9 but off for all other steps.

TABLE 2

Solenoid Control Sequence For Standard Perfusion

| Sub-Task Accomplished | 00*0* | 1 | 2 | 3 | 4 | 5 | 6 | 7 | 8 | 9 | 10 | 11 | 12 |
|---|---|---|---|---|---|---|---|---|---|---|---|---|---|
| 1. Initial recirculation to R1 | − | − | − | − | − | − | − | − | − | + | − | − | − |
| 2. R1 gradient | Same as 1, but activate SR1 ||||||||||||| 
| 3. From R2 just to F1, no recirculation** | + | − | − | − | − | − | − | + | − | − | − | − | − |
| 4. Deliver R2 first solution through F2, no recirculation | + | − | − | − | + | + | − | − | + | − | − | − | − |
| 5. Recirculate R2 solution except from organ | + | − | − | − | + | + | − | − | + | − | + | − | − |
| 6. Recirculate all R2 solution | + | − | − | − | + | + | − | − | − | − | + | − | − |
| 7. Run a gradient from reservoir R2‡ | Same as 6, but activate SR2 ||||||||||||| 
| 8. Perfuse from R3 just to S6/F2** | − | − | + | + | + | − | − | + | − | − | − | − | − |
| 9. Perfuse from R3 to F3, circuit open | − | − | + | + | + | + | + | + | − | − | − | − | − |
| 10. Recirculate to R3 through F3, circuit partially open | − | − | + | + | + | + | + | + | − | − | − | + | − |
| 11. Recirculate all R3 fluid | − | − | + | + | + | + | + | − | − | − | − | + | − |
| 12. Run first part of R3 gradient | Same as 11, but activate SR31 ||||||||||||| 
| 13. Run second part R3 gradient*** | Same as 11, plus SR31 and SR32 ||||||||||||| 
| 14. Open circuit, perfuse from R4 through F3 | − | + | + | + | + | + | + | + | − | − | − | − | − |
| 15. Recirculate to R4 except from organ | − | + | + | + | + | + | + | + | − | − | − | − | + |
| 16. Recirculate from both loops to R4 | − | + | + | + | + | + | + | − | − | − | − | − | + |
| 17. Run R4 gradient | Same as 16, but activate SR4 |||||||||||||

*For normal perfusions, solenoids S0, S00, and S13–S16 will always be non-actuated.
**This step prevents fluid from the previous reservoir, which is initially present in the line between the new reservoir and the filter that had been previously equilibrated with fluid from the new reservoir, from contaminating the previously equilibrated (new) filter.
***As noted in the discussion, SR32 activation must follow a duty cycle initially, ending in permanent activation of SR32 until end of use of R3. The duty cycle involves switching back and forth between solenoid patterns 12 and 13 as dictated by the duty cycle requirements.
‡Step 7 is optional.

The number of reservoirs could be less than or greater than the number specified here, with corresponding changes in solenoid number. Furthermore, the number of layers of R1–R4 need not conform to the descriptions given above. The limits would be one reservoir at the least and perhaps eight reservoirs at the maximum, in which any reservoir could have from one to four compartments. The upper limits are based partly on volume and crowding constraints and partly on the difficulty of imagining any procedure complex enough to require more reservoirs for its control.

Another variation would be to employ different capacity reservoirs at different positions (e.g., instead of the herein preferred embodiment, one might have a 2-liter reservoir followed by a one-liter reservoir followed by a 3-liter reservoir followed by a one-liter reservoir, and so on).

In principle, the use of individual reservoirs could be abandoned in favor of one multicompartment reservoir consisting of perhaps four to twenty concentric cylinders each activated by solenoids or even by manual levers external to the temperature-controlled area, all stirred by a single central stir table. Abrupt or step changes in concentration could still be accommodated if the stepped change is not delivered via the stirred central area. The relative positions of the reservoirs could also change.

The arterial concentration sensor could be located proximal to rather than distal to the origin of the organ loop in the circuit, but should not be located proximal to the filters.

A pressure sensor to sense pressure developing on the circuit pump side of the filters could be incorporated as a warning device.

More generally, the device could be separated into two devices, the first for preparing organs for cryopreservation and the second for preparing previously cryopreserved organs for transplantation. The first device would omit R3 and R4 (and associated solenoids) while the second would omit R1 and R2 (and associated solenoids) while otherwise being substantially the same as the unified device. Given that cryopreservation and the recovery from cryopreservation may occur at different locations and under the direction of different individuals, this variation is likely to be of use under practical conditions. Essentially, these two devices would be identical except for the use of different software and the use of different reservoirs for adding and for removing cryoprotectant. Another usage could involve the unorthodox use of only two reservoirs to accomplish both loading and unloading; for example, loading could be done using R1 and R3 if only the inner compartment of R3 were used (R3 standing in for R2), and unloading could be done using R1 and R3 if R1 is substituted for R4.

The above-described equipment for the introduction and removal of cryoprotective agents has been summarized elsewhere by Fahy (see, *Biomed. Instrumentation Technol.* 28:87–100 (1994)). This equipment, described above in the first embodiment, has been successfully used to permit mammalian kidneys and livers to be perfused with vitrifiable media with life support function after transplantation.

Subsequent to the invention of the embodiment described above, the present inventor has discovered a further embodiment that is described in detail below. It has been surprisingly learned that the ideal procedure for introducing concentrations that can vitrify without the application of hydrostatic pressure involves organ perfusion at temperatures in the vicinity of −20° to −40° C. (usually −20° to −30° C.) (see, Fahy et al., patent application No. 08/292,001, filed Aug. 18, 1994, now U.S. Pat. No. 5,723,282, the disclosure of which is incorporated herein in its entirety by reference). To accomplish perfusion within this temperature range, it has been necessary to remove the organ from the perfusion machine, immerse it in pre-cooled perfusate, and to continue perfusion and any further temperature reduction under manual control, returning the organ to the perfusion machine only after manual warming. These manual steps are not only inconvenient, but they are hazardous, presenting numerous opportunities for error. This inconvenience and, most importantly, the hazardousness of manual manipulations could discourage widespread use of organ cryopreservation. Therefore, since the equipment previously described was not designed to accommodate these extensions of the original protocol, modifications are needed to permit these additional steps to be accomplished by the equipment and the associated software without manual intervention. Similarly, it is hazardous for technicians to remove organs from the perfusion machine following their perfusion with vitrifiable media. It is therefore desirable to allow organs to be further cooled or even vitrified, within the apparatus, and modifications to permit achieving this goal are therefore desirable.

Certain difficulties present themselves in contemplating perfusion at −20° to −40° C. within the equipment. These include (1) how organ perfusion at −25° C. or so can be carried out;

(2) how organ temperature can be kept uniform when organ flow rate drops so low as to render arterial cooling ineffective in controlling organ temperature; and (3) how organ temperature can be changed in steps from, for example, −3.5° C. to −25° C. to, if desired, −40° to −60° C. and then back to −3.5° C.

The solutions to these problems as well as the problem of vitrifying or nearly vitrifying the organ within the previously-described equipment and modifications of the method of operation of the equipment are described below with reference to the second embodiment of this invention.

Figure 5:
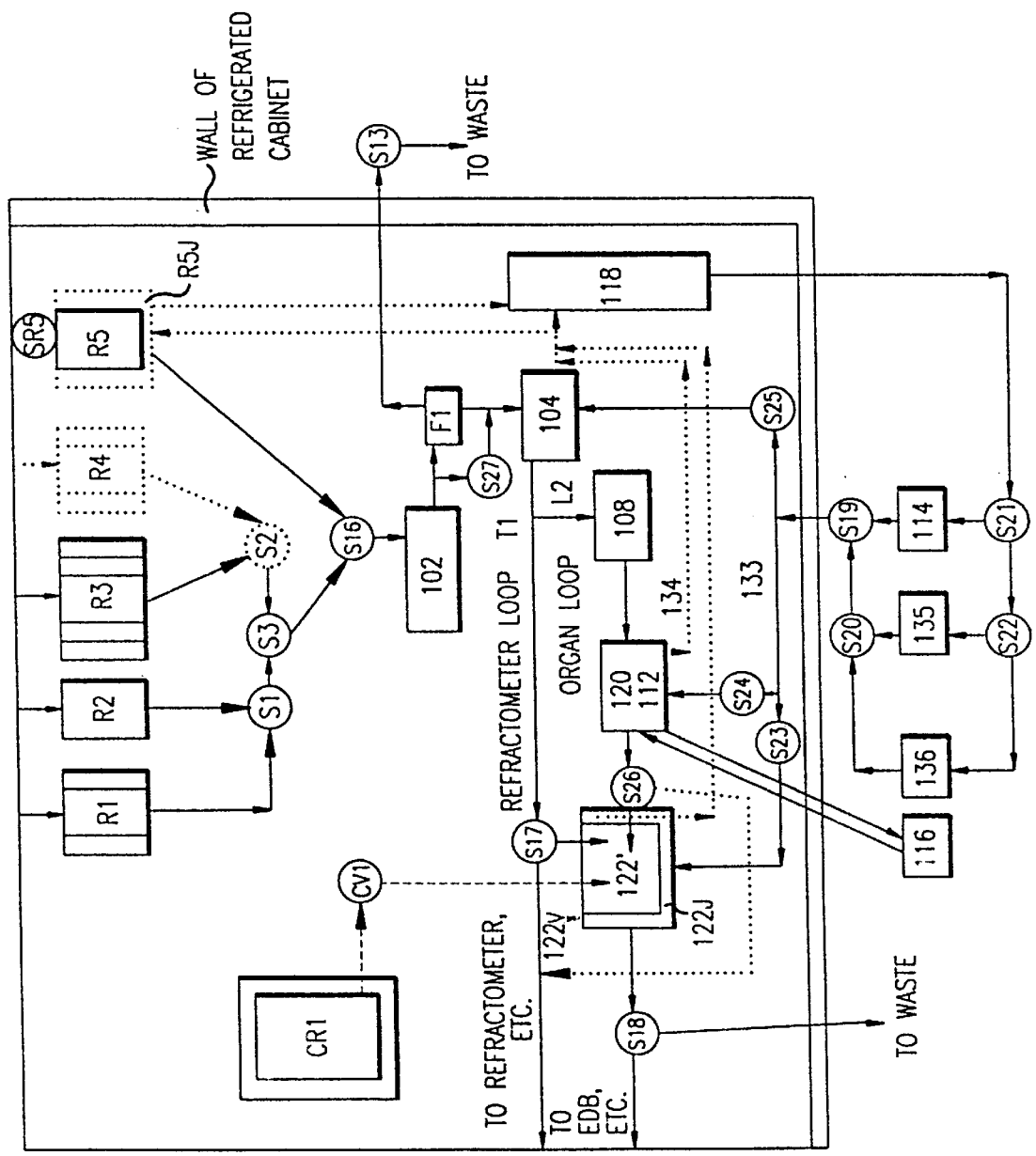
FIG. 5 shows a modification to the organ perfusion apparatus of FIG. 1 which comprises much of the present invention.

The second embodiment of this invention is best described with reference to FIG. 5. FIG. 5 represents a modified portion of FIG. 1. FIG. 5 omits for the sake of clarity certain details shown in FIG. 1 (including quick disconnects; the option of having more than one filter; the manual clamps on R1–R4; the filter vent bypass; the cleaning ports C1–C4 and their associated lines, solenoids, the filters; solenoids that control R1, R3, and R4; and all circuit elements upstream of the reservoirs and downstream of the organ container and the beginning of the refractometer loop). Common circuit elements shown in both figures have the same reference designations (e.g., reservoirs 1–4 (R1–R4), reservoir sampling solenoids S1–S3, the circuit pump 102, the filter F1, filter vent solenoid S13, common circuit heat exchanger 104, solenoid holding block 118, the organ loop L2, the "T" junction T1 between L2 and the refractometer loop, the organ pump 108, the organ loop heat exchanger 112 (shown in conjunction with the bubble trap/mixer elements 120 which are incorporated with it into a single unit), the cold bath 114 and the warm bath 116, and the organ container 122). All elements shown in FIG. 5 are to be understood as being contained within the circuit as otherwise shown in FIG. 1. The specific modifications to the perfusion circuit required by the current invention and shown in FIG. 5 are described in detail below.

The cooling system has been modified in the embodiment of FIG. 5. In the embodiment of FIG. 1, a single cold bath 114 was employed. The cold bath 114 provided coolant to heat exchanger 112, the effluent coolant of which provided cooling for main circuit heat exchanger 104, the effluent coolant of which in turn provided cooling for the solenoids located in the solenoid holding block 118, the effluent coolant of which returned to cold bath 114. In the embodiment of FIG. 5, cold bath 114 is connected via a valve S19 (which may be a solenoid valve, a pneumatically-controlled valve, a motorized valve, or, less desirably, a hand-operated valve) and through cooling lines 133 to 3 parallel target objects, i.e., the heat exchanger 112, the heat exchanger 104, and a jacket 122J of organ container 122'. These objects must be cooled in parallel rather than in series in order to assure that each reaches the same common final temperature. Temperature near-equality in heat exchangers 104 and 112, and jacket 122J is essential for the effective operation of this embodiment. Drainage lines 134 (dotted) carry effluent coolant from heat exchangers 104 and 112, and jacket 122J to solenoid cooling block 118 either directly or, in an alternative embodiment, after first being used for preliminary cooling of the contents of a new reservoir R5 via a jacket (R5J) surrounding reservoir R5. Coolant removed from cold bath 114 is returned to bath 114 via a valve S21 similar in concept to valve S19.

In this embodiment, cold bath 114 is normally set to approximately −9° C. as in the first embodiment. When it is time to lower temperature to about −25° C., valves S19 and S21 are activated. This permits low temperature bath 135 to be sampled rather than bath 114, and causes effluent coolant to pass from cooling block 118 to bath 135 rather than to bath 114. The temperature in bath 135 is set to approximately −30° C. so as to achieve temperatures in heat exchangers 104 and 112, and jacket 122J of about −25° C. after accounting for heating of the fluid from exposure of the coolant lines to room temperature air in transit. If further cooling below −25° C. is desired after introducing, in that temperature vicinity a concentration of cryoprotectant that is sufficient to vitrify, valves S20 and S22 are activated without deactivation of valves S19 and S21 so as to open a flow path from block 118, through valves S21 and S22 into bath 136, and through valves S20 and S19 to cooling lines 133 and ultimately back to block 118. This allows bath 136 fluid to be withdrawn and returned to bath 136. Bath 136 is normally set to a temperature below −40° C. (often approximately −55° C.). It will be seen that valves S19, S20, S21 and S22 are directional flow control valves which control the direction in which fluid flows through them.

The organ container jacket 122J is a part of the modified cooling system. It is cooled by being filled from the bottom and drained from the top. The jacket is normally filled only when the organ is to be cooled to below −10° C. and is allowed to fill by opening a programmable occluding valve S23.

Because the resistance to coolant flow through jacket 122J is expected to differ from the resistance to coolant flow through heat exchanger 112 and 104, occluding valves S23, S24, and S25 are installed to force coolant to flow through any channel that otherwise may have its coolant "stolen" by flow through any or both of the other two channels. Valve S23 is chosen to be normally closed, and is opened only by active actuation, to prevent excessive cooling during perfusion of the organ with low concentrations of cryoprotectant, whereas valves S24 and S25 are chosen to be normally open, and each is occluded only if and when necessary to force fluid through one or both of the other two channels. Such occlusion at valves S24 and S25 is carried out only briefly to prevent warming of the channel being occluded, and is intended only to ensure adequate flow through all three coolant pathways, as determined by temperature sensors (not shown) installed in each of the three target objects heat exchangers 104 and 112, and jacket 122J.

The embodiment of FIG. 5 shows a new solenoid valve S16 used to allow fluid to flow to the organ either from the traditional set of reservoirs R1–R4 or from a reservoir R5. In the embodiment of FIG. 1, vitrifiable media was present in reservoir R2. In the embodiment of FIG. 5, reservoir R2 contains an intermediate concentration (presently the best concentration is considered to be approximately 44% w/v of the previously-described mixture of dimethyl sulfoxide, formamide, and 1,2-propanediol [44% w/v D(1)FP$_{13.47}$], acceptable limits being 35%–50% w/v cryoprotectant of whatever nature) of cryoprotectant. Reservoir R5 contains the concentration that will be used to render the organ vitrifiable. The concentration present in reservoir R2 must be sufficient to reduce freezing point to the target temperature chosen for perfusion with the vitrification solution present in reservoir R5. In the process employed with the system of FIG. 5, this perfusion temperature is −25° C. (acceptable limits being −10° to −35° C.), and 44% w/v D(1)FP$_{13.47}$ has a freezing point near −28° C., which is sufficient to permit cooling to −25° C. without danger of crystallization. Note also that reservoir R5 is equipped with an optional cooling jacket, a reservoir feature not present in the previously-described embodiments but which is important in the current embodiment to ensure complete cooling of perfusate from R5.

The embodiment of FIG. 5 includes a valve S17, which, when activated, diverts fluid from the refractometer loop to the organ container 122'. Valve S17 is in practice located as close as possible to circuit heat exchanger 104, and actuation of valve S17 therefore bathes the organ in cryoprotectant that has been cooled to the target temperature (e.g., −25° C.) by passage -through 104 at the same time the organ container 122' is cooled as well by passage of fluid at the same temperature although its jacket 122J. Bathing the organ in a bath of a desired temperature while maintaining the bath temperature via continuous circulation through jacket 122J provides a uniform organ temperature for perfusion that is reinforced by perfusion with the same temperature perfusate as established by cooling the organ loop perfusate at heat exchanger 112.

Another important component of the fluid handling system of this embodiment is a valve S18, which is able to drain fluid from organ container 122' and send it to waste. Valve S18 is used in order to prevent fluid bathing the organ from being reintroduced to the circuit when it is time to change to a different perfusate. It is also very important for draining cryogen from organ container 122' in applications requiring organ vitrification or near-vitrification within organ container 122'. Valve S18 is a directional flow control valve. It is normally oriented to direct fluid from the container 122' through the circuit containing effluent distribution block 124, etc. Valve S18 diverts fluid to waste only when specifically activated. It is used when (a) direct drainage of organ container 122' is faster and/or significantly less contaminating of the circuit than direct pumping via the recirculation pump 128 or (b) when it is preferred for any other reason over drainage by means of the recirculation pump 128.

A valve S26 allows fluid in the dead space of the organ loop, between T1 and container 122', to be discarded or recirculated. This is particularly important during controlled washout of R5 perfusate from the organ upon switching to reservoir R3 as described below.

Another valve S27 allows the filter F1 to be bypassed if required by extreme viscosity of the R5 perfusate at circa −10° to −35° C. It can be activated in response to elevated presssure sensed between pump 102 and F1 (sensor not shown).

As shown by the dotted line represesentations of reservoir R4 and solenoid valve S2, these elements may be omitted from this embodiment. In the approach of this embodiment, the low molecular weight and high molecular weight osmotic buffering agents present at the end of cryoprotectant elution with R3 are not removed prior to transplanting the organ (or, for livers, are not necessarily present at all to be removed). Therefore, there is no necessity for R4 to contain the same solution ultimately delivered from R3 at the end of the cryoprotectant elution. On the other hand, R4 may, in the present embodiment, contain additional perfusate of composition identical to that normally present in the inner compartment of R3, which is used to remove vitrifiable concentrations of cryoprotectant and introduce osmotic buffers, for reasons described below.

The embodiment of FIG. 5 also includes a cryogen reservoir CR1 and its associated cryogen valve CV1. These components need not be located within the refrigerated cabinet. In the preferred mode, reservoir CR1 is located within the refrigerated cabinet and is filled manually just prior to use.

The process of equipment control for carrying out the method for organ perfusion with vitrifiable media using the system of FIG. 5, is described in the flowcharts of FIGS. 6A–D. The accompanying changes in the actuation patterns of the solenoid valves and similar-acting valves required to follow the flowcharts of FIGS. 6A–D are further described below.

Figure 6A:
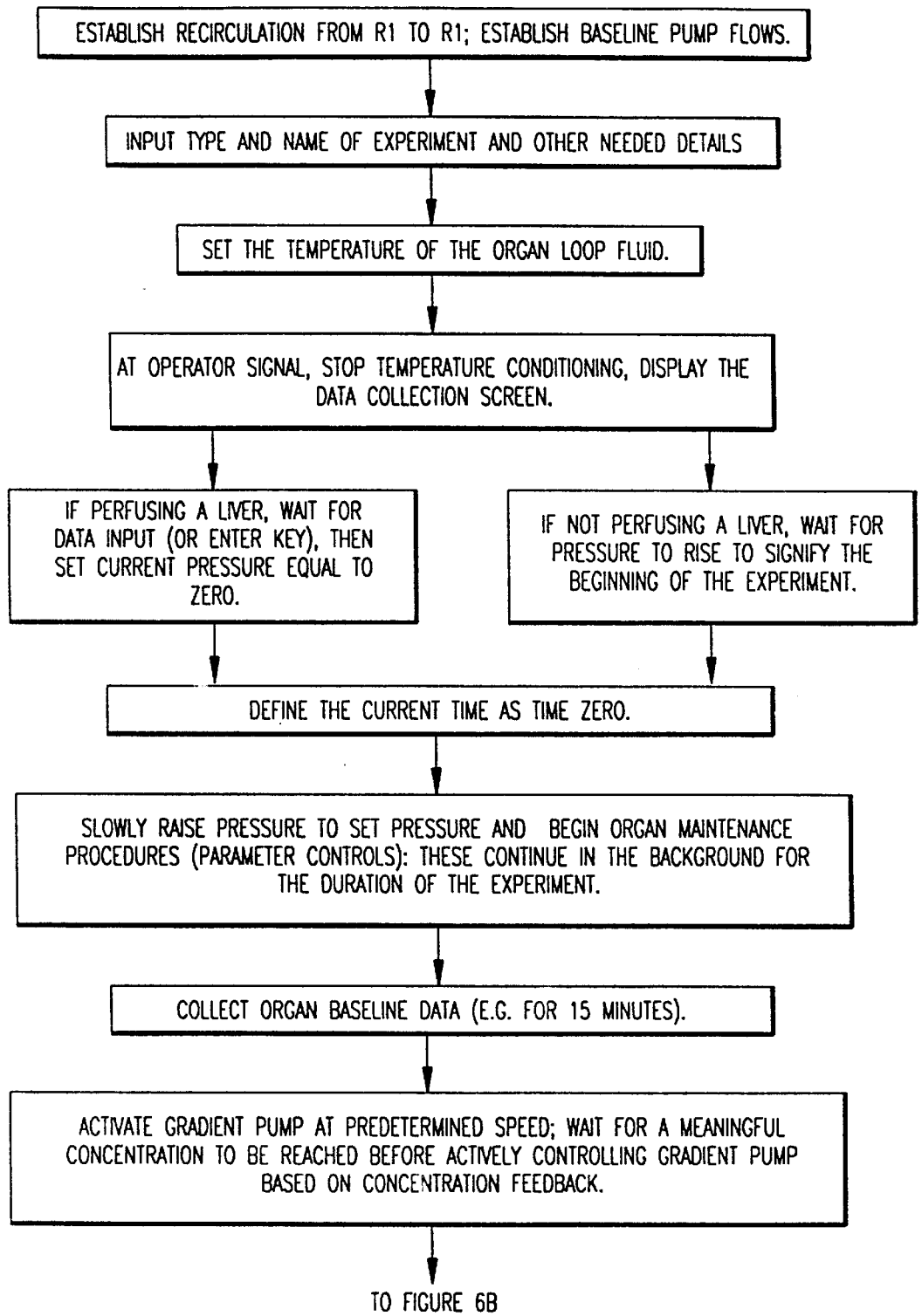
FIGS. 6A–D comprise a flow chart of activities for organ cryoprotectant perfusion for the present invention.
Figure 6B:
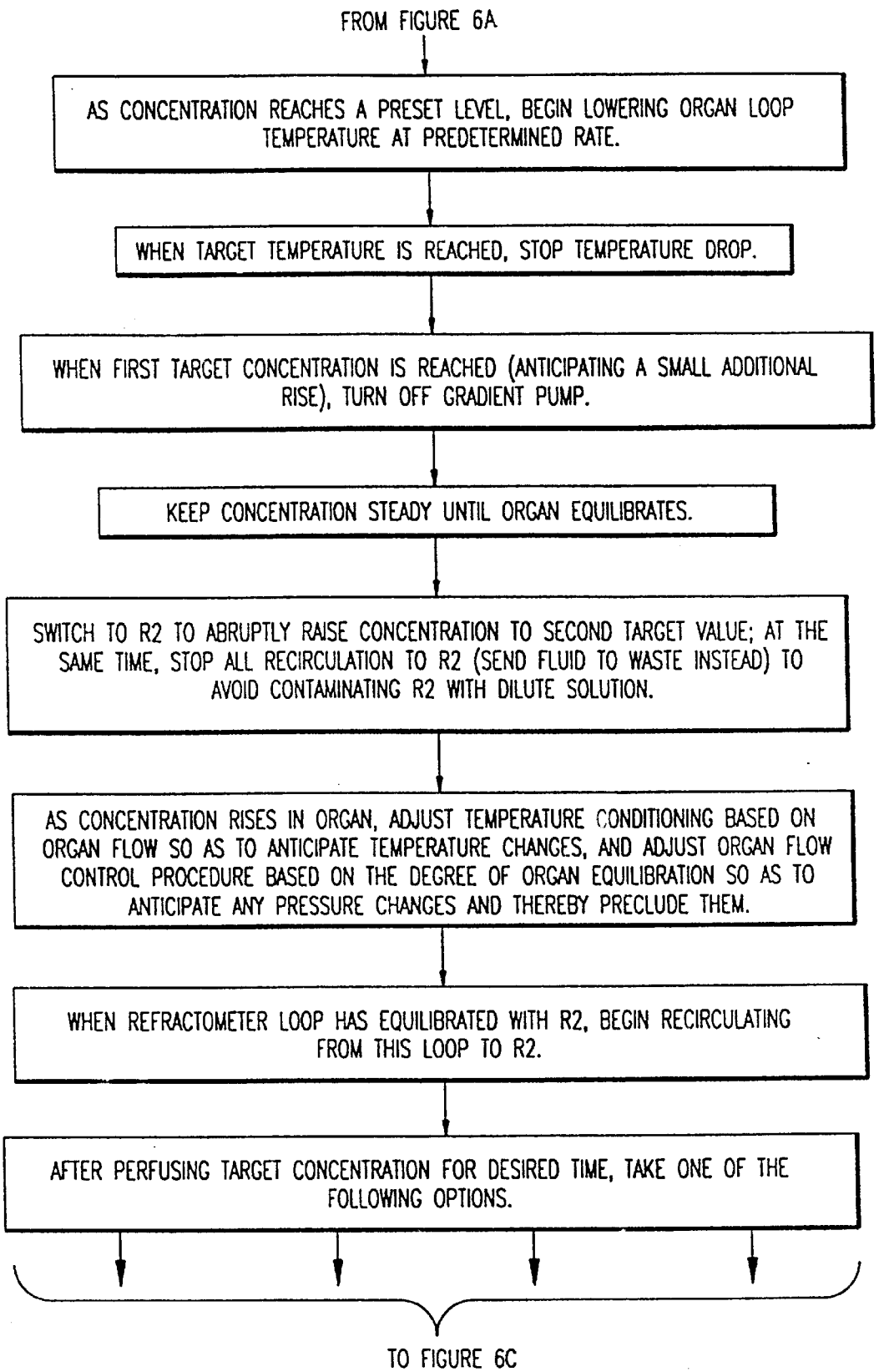
Figure 6C:
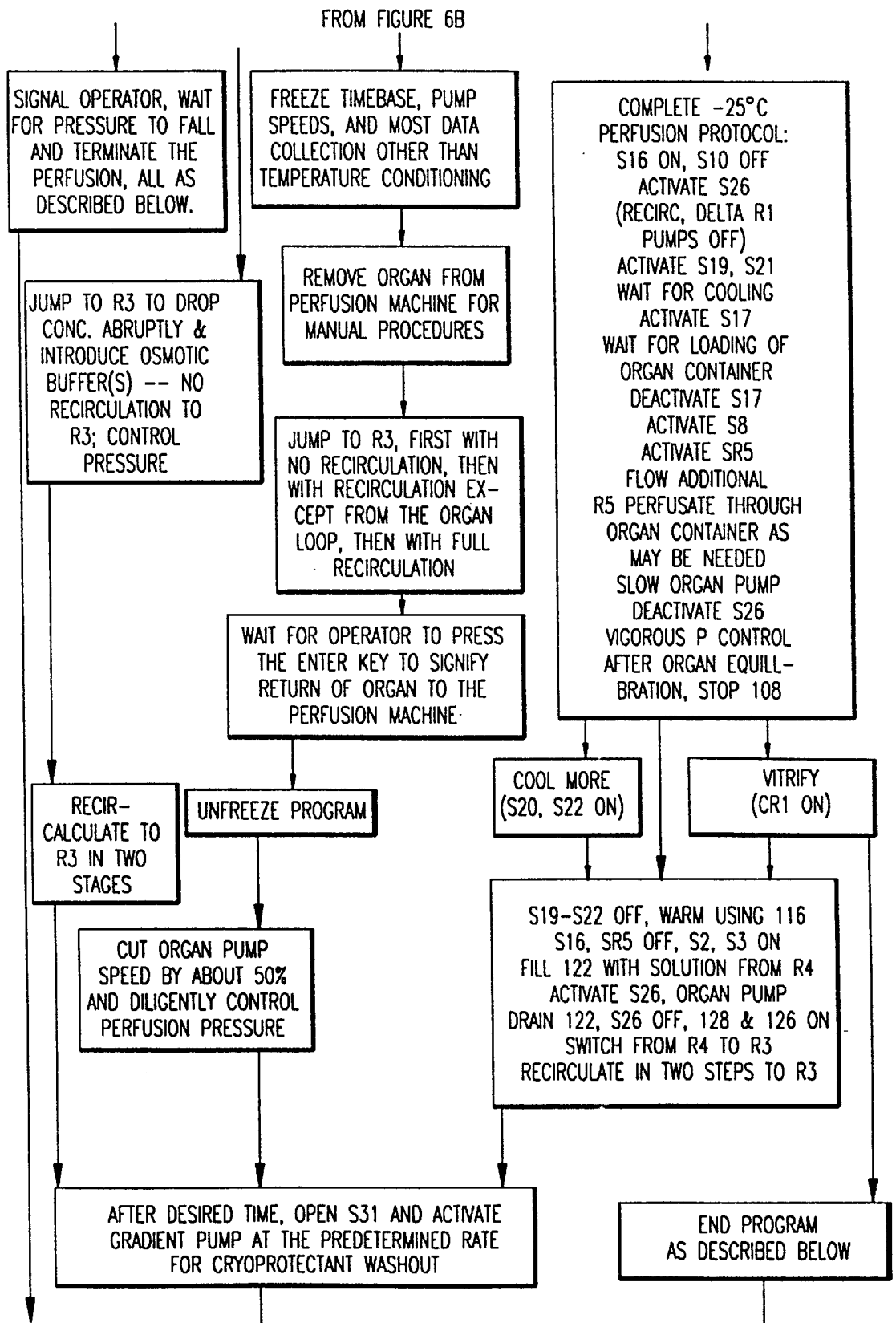
Figure 6D:
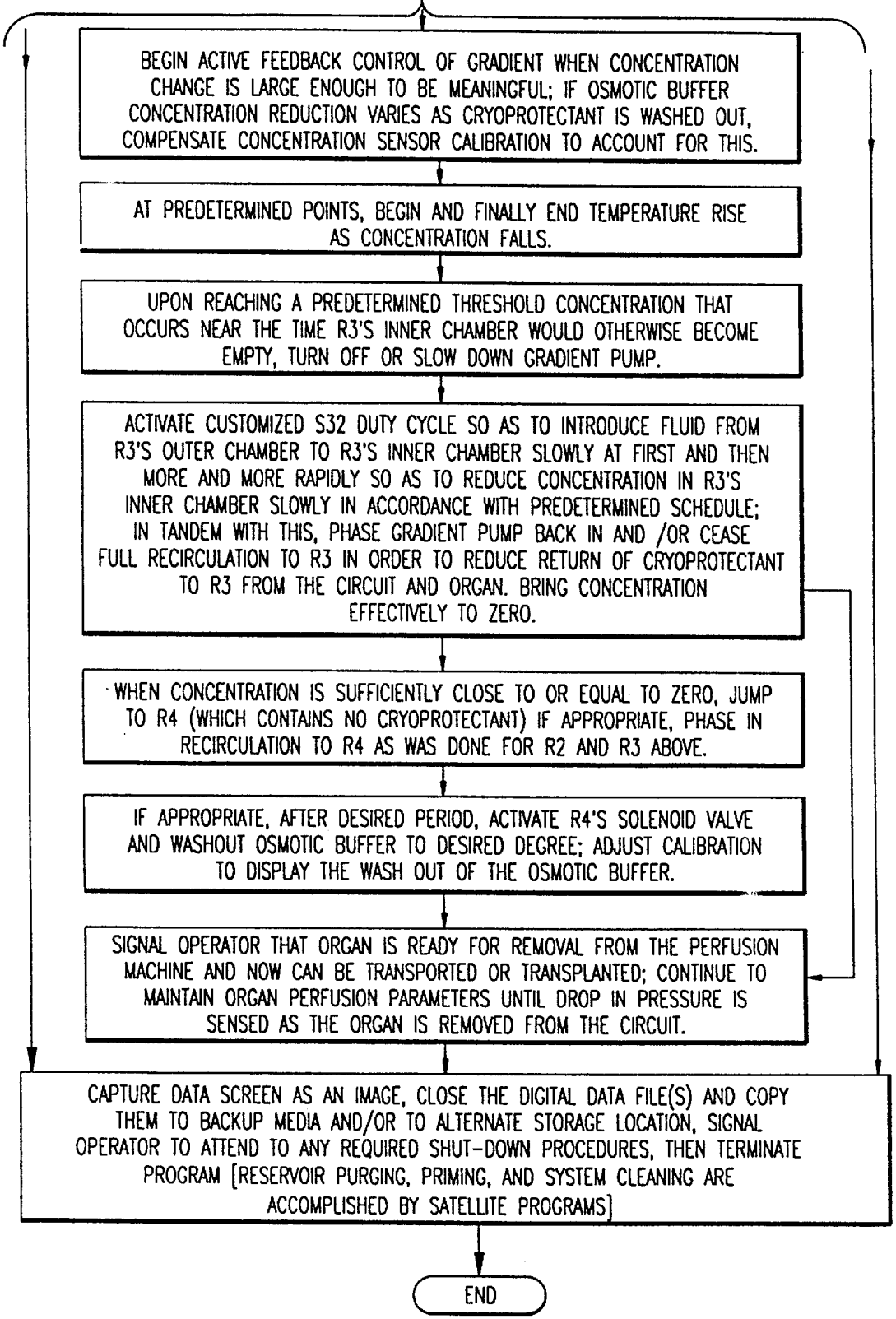

The normal protocol as described in FIGS. 6A and 6B is followed until the steps required for controlling the deep cooling, low temperature perfusion, and warming steps are required (FIG. 6C). Following these steps, the program reverts back to the standard methodology for removing cryoprotectant (FIG. 6D). Only the unique steps of FIG. 6C (rightmost column) are described here.

Step 1. Begin Delivery Of Vitrification Solution. At the end of equilibration with the contents of R2, valve S16 is activated and solenoid S10 is deactivated. (Depending on the operating temperature range of S16, it may be a solenoid valve or other type of actuatable valve capable of acting on fluids of the viscosity and temperature of the contents of R5, similarly to the concept of valves S19–S25). This actuation of valve S16 causes fluid from reservoir R5 to be sampled by circuit pump 102 and delivered to the refractometer loop and to the organ loop. Deactivation of valve S10 allows fluid to flow to waste rather than being directed into reservoir R2, which prepares the circuit for eventual recirculation back to reservoir R5.

Depending on the size of the filter F1, sufficient surface area may or may not be available in filter F1 to accommodate the standard rate of flow from pump 102 without exceeding advisable pressure limits between pump 102 and filter F1, given the increased viscosity of R5 perfusate caused by the higher concentration of cryoprotectant in reservoir R5 in combination with precooling of the R5 perfusate if the R5 temperature-conditioning jacket R5J is in use. Problems with passing the required volume flow through filter F1 can be controlled by (a) using a larger filter size; (b) bypassing filter F1 by actuation of optional valve S27 (this has been shown to be acceptable by the success of the manual process for perfusing kidneys with 8.4 M cryoprotectant described in application Ser. No. 08/292,001, now U.S. Pat. No. 5,723,282); or (c) reducing the speed of pump 102 (preferably under command of the computer controlling the process).

Step 2. Divert Flow Away From Organ. Shortly after activation of valve S16 and before fluid from reservoir R5 has time to reach the organ container 122', valve S26 is activated. This prevents the organ from perfusing with the contents of reseervoir R5 before the organ has been previously cooled to the target temperature range described above. The continuation of flow through the organ loop L2 to valve S26 ensures that passive warming of otherwise-stagnant perfusate in L2 during cessation of flow through the organ does not occur. The recirculation pump 128 and the delta R.I. pump 126 may also be turned off at this step because of the lack of fluid to recirculate.

Figure 7A:
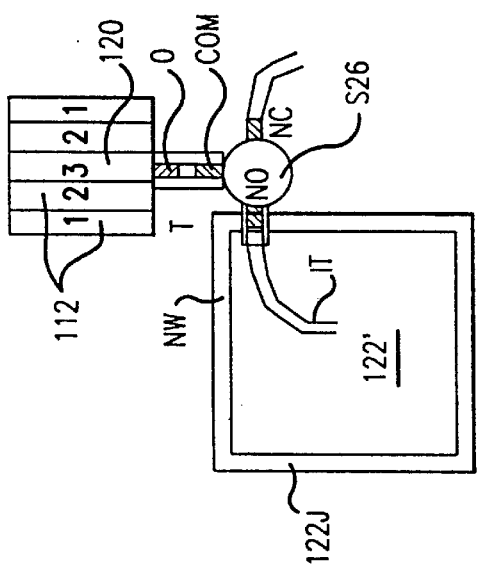
FIGS. 7A and 7B shows a detail of the organ container and associated cooling jacket and solenoid or other valve for controlling arterial perfusate temperature and composition to permit deep subzero cooling and subsequent further cooling or warming.
Figure 7B:
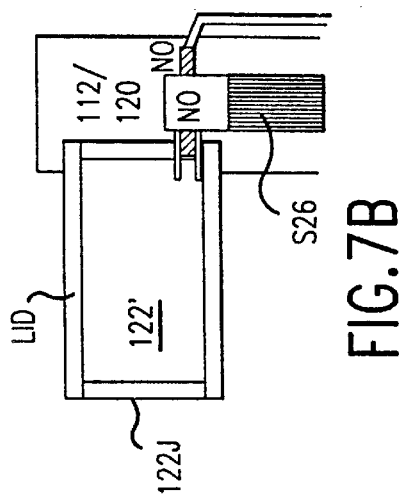

More detail concerning the specific arrangement of valve S26 is provided in schematic form in FIG. 7. Commercially-available solenoid valves tend to be configured as shown in FIG. 7, with the normally closed (NC) and the normally open (NO) paths emerging at right angles from the common (perpetually open) port (Com). This creates the need for a right angle turn in the fluid path upon proceeding from bubble trap 120 to organ container 122', which is mildly awkward in comparison to the standard linear path, wherein heat exchanger 112/bubble trap 120 are positioned directly facing the near wall (NW) of the organ container 122'. Although a more favorable valve geometry (180° angle between Com and NO parts) can be made for this invention, FIG. 7 depicts the geometry that is commonly available, which is workable.

As noted in FIG. 7, one of valve S26's sidearms protrudes into the wall of organ container 122', penetrating through the jacket region 122J. The heavy lines surrounding the NO sidearm in FIG. 7 represent silastic or similar tubing that is permanently bonded into organ container 122' and jacket 122J to form a leakproof, open port through jacket 122J with flexible walls that can make a leakproof seal against the NO sidearm when it is inserted into this port. Similarly, internal tubing IT, into which the arterial cannula ligated onto the organ's artery or portal vein can be inserted distally, also forms a leakproof seal at this port. The portion of valve S26 that heats up (in the case when the solenoid is a heat producing type) is oriented downwards and away from the organ container and is spaced an appreciable distance from heat exchanger 112/bubble trap 120. Consequently, the use of solenoid valves will not cause a serious heating problem.

An alternative to the use of valve S26 could be docking between organ container 122' and heat exchanger 112/ bubble trap 120 such that there is no air gap and hence no fluid gap between organ container 122' and heat exchanger 112/bubble trap 120 that would otherwise be subject to passive warming during cessation of organ flow induced by the need to set the speed of organ pump 108 to zero to avoid premature organ perfusion with vitrifiable media. Only the fluid between T1 and heat exchanger 112/bubble trap 120 would indeed warm up passively, and this fluid could be recooled by passage through 112 on the way to the organ. Upon resumption of organ flow, fluid from reservoir R2 that was previously not rinsed out of the organ loop would enter the organ prior to the fluid from reservoir R5, but this would be of little consequence. During cessation of flow, the perfusate within heat exchanger 112 would tend to cool to a lower-than-desired temperature due to the extra time available for complete heat exchange, and this overly cold solution would be perfused toward the organ upon resumption of flow, but this problem is also considered minor. The most important reason why the use of valve S26 is preferred to the use of a close docking between organ container 122' and heat exchanger 112/bubble trap 120 is derived from consideration of the washout of vitrification solution and is described below.

The ability to plug valve S26 into the port of organ container 122'/jacket 122J provides the arterial quick disconnect feature of container 122'/jacket 122J that is desired for easy removal of container 122'/jacket 122J for cleaning or replacement, while leaving valve S26 and heat exchanger 112/bubble trap 120 in place.

Step 3. Initiate Deep Cooling. Valves S19 and S21 are activated, allowing deep cooling of the perfusate to occur at heat exchange elements 104 and 112, and jacket 122J by allowing cold bath 135 coolant to be delivered through delivery lines 133. During deep cooling, reservoir R2 fluid between T1 and valve S26 is replaced by fluid from reservoir R5 and discarded through valves S26 and S9-SR5 to waste (pump 108 remains on at a low pump rate). Valve SR5 is located in the line between valve S12 and the waste outlet and operates similarly to S9–S12.

Step 4. Bathe Organ In Cold Fluid. After a time delay of approximately 15 to 300 seconds, valve S17 is activated. This activation of valve S17 causes the organ container 122' to begin filling with pre-cooled perfusate from reservoir R5. The time delay selected is judged on the basis of two competing concerns. First is the concern that premature transfer of fluid from the refractometer loop to organ container 122' will cause container 122' to fill with liquid that is warmer than the target immersion temperature. In addition to inducing slower than desired cooling, this fluid must be removed via valve S18 or the effluent recirculation pump and replaced with subsequent, colder fluid from the refractometer loop in order to attain the ultimate degree of cooling necessary prior to the introduction of R5 perfusate through the organ. The contrary concern is that cessation of organ flow will allow passive warming of the organ to take place, which is not desirable. (This will be minimized by filling jacket 122J with cold fluid, but the air temperature in container 122' will initially remain warmer than the target low-temperature perfusion temperature). In practice, 15–300 sec. generally will be required for organ warming to become measurable, and 15–300 sec. will generally be required for the fluid flowing in the refractometer loop to attain the desired temperature imposed by cooling at heat exchanger 104 from cold bath 135. In practice, the distance between valve S17 and heat exchanger 104 is very small, on the order of 2–6 inches, and the speed of fluid flow between heat exchanger 104 and valve S17 is relatively high, so that passive warming of perfusate in transit from heat exchanger 104 to valve S17 is not appreciable.

Temperature similarity at heat exchangers 104 and 112, and jacket 122J is essential in order to cool the organ to a controllable temperature by -external cooling (accomplished by cooling at heat exchanger 104 and at jacket 122J) and for this externally-applied temperature to be in agreement with the temperature of the fluid that is later flowing internally within the organ, which is controlled at 112.

Step 5. Stop Organ Container Drainage. If not already done, the organ effluent recirculation pump 128 is turned off either by the computer or manually in response to a computer prompt. This is necessary to allow organ container 122' to fill with fluid diverted into it by valve S17.

Step 6. Stop Organ Container Filling. After sufficient volume has been diverted into container 122' to cover the organ to a depth sufficient to ensure essentially complete cooling (generally 0.5–3 inches), valve S17 is deactivated, closing the fluid path into container 122' and allowing fluid to flow normally in the refractometer loop.

Step 7. Recirculate To Reservoir R5. Approximately upon deactivating valve S17, valve SR5 is activated to recirculate perfusate from reservoir R5 back to R5 to permit organ perfusion to continue without needless consumption of perfusate.

Step 8. Revise Organ Bath Temperature As Needed. If necessary, due to heat inleak from the lid of the organ container 122', or due to necessary prior opening of valve S17 before sufficient cooling of the refractometer loop, ambient temperature in container 122' is maintained by taking the following steps:

(a) Drainage of organ container 122' is initiated either by activating recirculation pump 128 (while temporarily inactivating SR5 until the organ loop is cleared of residual R2 perfusate) or by activating valve S18;

(b) Valve S17 is activated to deliver additional, colder R5 perfusate into container 122';

(c) The flow rate out of container 122' is adjusted to be equal to the flow rate into container 122' via solenoid S17 by adjusting the S17 duty cycle, the S18 duty cycle, the speed of the recirculation pump 128, or any combination of these controls, the effect being to exchange the R5 perfusate in container 122' with freshly cooled perfusate so as to overcome any heat flow into container 122' or any initially incomplete cooling.

Step 9. Perfuse The Organ At Deep Subzero Temperature. After the organ has cooled sufficiently close to the target low-temperature perfusion temperature (generally, cooling will require 5–30 min. from the time of actuation of S17, 5 min. being the preferred time interval for small animal organs and longer times being required for more massive organs such as human organs), valve S26 is deactivated, and the flow through organ pump 108 is set to approximately 25% of the previous flow rate (acceptable limits being about 5% to 100% of the previous flow rate), a rate chosen to prevent pressure excursions above the desired perfusion pressure (generally 20–60 mmHg and preferably 30–50 mmHg, or 50–400% of the previous perfusion pressure depending on the type of organ and the species of origin).

Step 10. Adjust Arterial Perfusion Pressure. Arterial perfusion pressure is systematically adjusted to the desired level in the usual fashion.

Step 11. Allow for Organ Equilibration. Sufficient time is allowed for organ equilibration with R5 perfusate. Generally, this will require 30–90 minutes. During this time, ureter, bile duct, or other duct fluid is collected manually for CPA content or is diverted to the differential refractometer for automated tracking of concentration. Because the organ is immersed and drainage from 122' is blocked, delta R.I. cannot be followed in the normal way during this equilibration period. If a ductless organ, such as a heart, is being perfused or if standard, previously measured equilibration times are known, then time and flow rate alone are used to determine when equilibration is complete.

Step 12. Stop Organ Perfusion. Organ flow rate is set to zero.

Step 13. Cool Organ Further. If additional cooling is desired to the range of approximately −30° to −60° C. or lower, then the following steps are carried out:

(a) S20 and S22 are activated (dropping out bath 135 and initiating the use of bath 136);

(b) Drainage of organ container 122' is initiated either by activating recirculation pump 128 or by activating valve S18;

(c) S17 is activated to deliver R5 perfusate at the newer, lower and/or falling temperature into container 122';

(d) The flow rate out of container 122' is adjusted to be equal to the flow rate into container 122' via valve S17 by adjusting the S17 duty cycle, the S18 duty cycle, the speed of the recirculation pump 128, or any combination of these controls, the effect being to exchange the relatively "warm" (circa −25° C.) R5 perfusate in container 122' with colder (circa −30° to −60° C.) perfusate so as to smoothly but rapidly lower temperature to the desired final value.

Step 13 is particularly valuable when the object is to study the phenomenon of cooling injury or to store organs at non-vitrifying temperatures.

Step 14. Cool To Below −40° to −60° C. If the organ is to be vitrified or nearly vitrified in container 122', the following steps are carried out (and step 13 may be omitted):

(a) S17 is deactivated;

(b) The organ and its associated cannula(e) are manually detached from the arterial perfusion line using forceps or hemostats to avoid warming the organ or its surrounding liquid;

(c) A relatively small container for storing and later warming the organ is filled with R5 perfusate by being immersed in container 122', and the organ and any holder associated with it are placed into this storage/warming container, again using a non-touch technique;

(d) The storage/warming container is sealed;

(e) Container 122' is emptied by activating either valve S18 or the recirculation pump 128;

(f) Cryogen (typically, an inert fluorochemical precooled to approximately −130° to −140° C., particularly E-1 perfluoroether compound made by DuPont (which remains liquid to −160° C.) or Freon F-11 (which freezes at −111° C.), or a mixture thereof) is admitted to container 122' either manually or by means of an auxiliary cryogen reservoir CR1 drained directly into container 122' by the computer using a cryogenic solenoid valve CV1, which may be a valve similar or identical to the Liquid Nitrogen Solenoid valve 125 (catalog nos. HP80033 and 82E22LT) made by Automatic Switch Comapny (ASCO; Florsham Park, N.J.);

(g) By either leaving valve S18 open or allowing for valve S18 to be opened and closed intermittently, cryogen can continue to flow over the organ storage/warming container without overflowing the container 122' and while cooling the organ storage/warming container by full immersion, thus generating very efficient cooling. Cryogen can be collected manually by directing the S18 waste line to a recycled-cryogen container;

(h) As the cryogen is introduced, the bath fluid from bath 136 that occupies the jacket 122J should be prevented from either freezing or dropping below its glass tranistion temperature. For maximum flexibility of choice of bath fluids, this may be accomplished by draining jacket 122J by activating a drain valve (not shown) and removing vent plug 122V while closing valve S23. This procedure could be avoided by using ethylene glycol plus $H_2O$ as the bath 136 fluid ($T_g$~−130° C.), but the jacket 122J should be drained ultimately anyway to allow container 122' to be removed for cleaning at the end of the experiment, so S23b and 122V remain desirable. Vent plug 122V can be a tube occluded by a computer-actuable pinch valve for automatic use.

(i) After the organ is ready to transfer to the organ bank for long-term storage, the user is notified to remove the organ storage/warming container with tongs and transfer it quickly to a carrier vessel and then into the organ bank, and the program is terminated.

Step 15. Begin Warming. When it is time to warm the organ and remove the cryoprotectant, valves S19–S22 are inactivated to allow cold bath 114 to begin warming at heat exchangers 104 and 112, and jacket 122J is drained. Warm fluid from warm bath 116 is also delivered through the heating channels 402 of heat exchanger 112. No perfusate will be passing through the organ at this point.

Step 16. Circulate First Washout Solution. When the temperatures at heat exchangers 104 and 112 are sufficiently high to avoid freezing the initial washout fluid from the inner compartment of reservoir R3, valve S16 is deactivated, valve S3 or the combination of valves S3 plus S2 are activated, and valve SR5 is deactivated to allow R3 (or R4) perfusate to enter the refractometer loop and be discarded to waste through solenoids S9–S12. Valve S2 is activated along with valve S3 when reservoir R4 contains the same fluid as the inner compartment of reservoir R3. This is the preferred mode of operation to provide sufficient volume to fill container 122' (see below) without an excessive fluid level in the inner compartment of reservoir R3.

If valve S27 has been previously activated to bypass filter F1, it is inactivated at this time to permit continuous filter sterilization of the perfusate to resume.

Step 17. Prepare Organ Loop. While the organ is beginning to warm, valve S26 and organ pump 108 are activated. The speed of pump 108 is not changed in comparison to its speed at the end of organ equilibration with R5 perfusate at the low temperature perfusion temperature (circa –25° C.). This step removes cold R5 perfusate, which will often remain in loop L2, replacing it with warming solution of the desired composition. It is this step for which the availability of valve S26 is particularly important, because without it, there is no way to purge L2 without first disconnecting the organ which is undesirable unless the organ is being banked. When the organ has been cryopreserved and is being recovered, L2 can be pre-primed with R3 fluid and washout of R5 fluid from L2 will therefore not be necessary.

Step 18. Prepare To Warm Organ By Immersion. If the organ has not been banked, it remains in container 122' and remains immersed in cold solution. Therefore when the temperature in the refractometer loop near valve S17 approaches approximately –10° to –1° C. (–5° to –2° C. in the best mode), the organ container 122' is drained by the means previously described. (If the organ has been banked, it is warmed outside the apparatus described here.)

Step 19. Begin Warming Organ. Either before or after completion of step 18, valve S17 is activated to fill the organ container 122' with R3 (or R4, if identical to R3) perfusate at approximately –10° to –1° C. (about –5° to –2° C.) in the preferred mode of operation of this embodiment. As and if needed, the fluid bathing the organ in container 122' so as to warm it up to the target temperature for washout of R5 perfusate can be turned over in the manner described in steps 8 and 13.

If the organ being processed has been previously vitrified and warmed back to temperatures between –1° C. and about –40° C., its storage/warming container is submerged in the perfusate bath in container 122' at this time, the storage/warming container is opened, the organ and its holder are removed from the storage/warming container, and the organ's arterial cannula is reinserted into container 122''s inner tubing IT (FIG. 7), all using a non-touch technique, after which the storage/warming container is removed.

Step 20. Drain Organ Container. By about this time, L2 solution has been purged with R3/R4 solution and S11 or S12 is activated to recirculate this fluid to its reservoir of origin. Roughly 5–15 min. after the onset of warming by immersion in container 122', container 122' is drained of R3 fluid by valve S18 or by the recirculation pump, warming having been completed or nearly completed.

Step 21. Begin Cryoprotectant Washout. Valve S26 is deactivated, allowing perfusate to reach the organ. At this time, recirculation pump 128 and delta R.I. pump 126 are activated (if they were not previously activated), and active control of arterial pressure is instituted. Solenoid S8 is activated.

Step 22. Switch From R4 to R3 And Recirculate. Solenoid S2, if previously activated, is deactivated, allowing R3 fluid to be drawn from R3 rather than from R4, and solenoid S11 is activated, if not previously activated, to recirculate R3 fluid flowing in the refractometer loop back to reservoir R3.

Step 23. Complete R3 Recirculation. R3 recirculation is then made complete by deactivating solenoid S8. This takes place as the delta R.I. signal indicates the organ effluent is approaching the concentration of the perfusate, which will be about the time the washout gradient is to begin.

Step 24. Complete Cryoprotectant Washout. At this point, the program is back to the standard mode of operation, except that, at its end, it will remain with reservoir R3 rather than moving onward to reservoir R4.

While various embodiments of the present invention have been described above, it should be understood that they have been presented by way of example, and not limitation. Thus the breadth and scope of the present invention should not be limited by any of the above-described exemplary embodiments, but should be defined only in accordance with the following claims and their equivalents.

What is claimed is:

1. A computer controlled apparatus for perfusing a biological organ or tissue, comprising:

a programmable computer;

a plurality of arterial perfusate reservoirs, each having an input and an output;

means coupled to said computer and to said reservoirs for selectively sampling the contents of said reservoirs under the control of said computer;

an organ or tissue container for holding a biological organ or tissue, comprising an inner container for housing the organ or tissue and an outer jacket substantially surrounding said inner container;

a recirculating fluid flow path connecting selected outputs and the inputs of the plurality of reservoirs;

an organ or tissue flow path extending from the recirculating flow path to the inner container;

a pump located in said organ or tissue flow path and coupled to and controlled by said computer for withdrawing fluid from the recirculating flow path and delivering said fluid to one or more organs or tissues in said organ or tissue flow path;

at least one low temperature bath containing fluid at a temperature within a predetermined range;

a low temperature flow path for selectively connecting said at least one low temperature bath to said organ or tissue flow path upstream of said inner container and to said outer jacket;

main pump means interposed in said recirculating flow path and optionally coupled to and controlled by said computer for circulating perfusate from a selected reservoir through said recirculating fluid flow path;

sensor means coupled to the computer and interposed in at least one of the recirculating and organ or tissue flow paths, for sensing at least one of the temperature, pH, pressure and concentration of the fluid in the flow paths and to provide the sensed information to the computer;

means for selectively sending perfusate back to a selected one of said reservoirs from the recirculating flow path or diverting perfusate to a waste outlet as a function of information sensed by said sensor means;

a temperature-controlled cabinet for housing the reservoirs, flow paths and pumps to maintain organ or tissue and perfusate temperatures at desired levels;

a temperature controller for controlling the temperature of perfusate in said recirculating flow path; and immersion means for directing temperature controlled perfusate from said recirculating flow path into the inner container without first passing the perfusate through the organ or tissue to submerge the organ or tissue sufficiently to effect cooling or warming of the organ.

2. The apparatus of claim 1, further comprising:

at least one additional low temperature bath containing fluid at a temperature in a predetermined range that is lower than the temperature of fluid contained in said one low temperature bath; and means for selectively connecting said additional low temperature bath to said low temperature flow path to selectively connect said additional low temperature bath to at least one of said organ or tissue flow path upstream of said inner container and said outer jacket.

3. The apparatus of claim 1, further comprising:

means for varying the concentrations of chemical agents in the arterial perfusate; and means for generating increasing or decreasing concentration-time profiles of the chemical agents in the arterial perfusate to elevate the concentration of the chemical agents in the perfusate to any desired level and to return the concentration of the chemical agents to or approximately to zero.

4. The apparatus of claim 3, wherein the sensor means comprises:

first sensor means for determining the concentrations of chemical agents in the fluid flow paths and for determining the uptake of these agents by the one or more organs or tissues in said organ or tissue flow path; and second sensor means coupled to the computer and interposed in at least on of the recirculating and organ or tissue flow paths, for sensing at least one of the temperature, pH, and pressure of the fluid in the flow paths and to provide the sensed information to the computer.

5. The apparatus of claim 4, wherein the first sensor means comprises a refractometer.

6. The apparatus of claim 5, further comprising a differential refractometer for determining the difference in chemical concentrations between the arterial and venous sides of an organ or tissue in said organ or tissue flow path.

7. The apparatus of claim 1, further comprising at least one heat exchanger upstream of the container in the organ or tissue flow path and wherein the temperature controller comprises at least one heat exchanger located in the recirculating fluid flow path for optimizing temperature control of an organ or tissue during perfusion thereof.

8. Apparatus according to claim 1, further comprising computer controlled means for controlling the flow of fluid in said low temperature flow path between said at least one low temperature bath and said outer jacket.

9. The apparatus accordingly to claim 1, further comprising means for immersing the organ or tissue in pre-cooled cryogen to lower the organ or tissue temperature to near its glass transition temperature.

10. Apparatus for equilibrating organs or tissues with vitrifiable concentrations of cryoprotectant, comprising:

a container for holding a biological organ or tissue;

first means for introducing high but not vitrifiable concentrations of cryoprotectant into an organ or tissue in said container at a temperature of approximately 0° C. after passing the cryoprotectant through a temperature control means for controlling the temperature thereof;

immersion means for diverting cryoprotectant from said temperature control means into said container without first passing the cryoprotectant through the organ or tissue to cool the organ or tissue by immersion/conduction;

second means for subsequently introducing fully vitrifiable concentrations of cryoprotectant into the organ or tissue in said container at a temperature of approximately −10° C. or lower after a predetermined period of immersion cooling of the organ or tissue without perfusion via said immersion means; and means for cooling the fully vitrifiable organ or tissue to a temperature of between −40° C. and −60° C. to vitrify or nearly vitrify the organ or tissue.

11. Apparatus according to claim 10, further comprising means for removing fully vitrifiable concentrations of cryoprotectant from the organ or tissue in a temperature range of between about −1° C. and −10° C.

12. Apparatus according to claim 11, wherein the first and second means include an organ or tissue flow path and the apparatus further comprises means to purge stagnant cryoprotectant from the organ or tissue flow path to avoid perfusion of the organ or tissue with said stagnant cryoprotectant.

13. Apparatus according to claim 10, wherein said cooling means comprise:

a plurality of individually addressable low temperature baths;

at least one heat exchanger selectively coupled to said low temperature baths; and a jacket substantially surrounding said container and selectively coupled to said low temperature baths.

14. Apparatus according to claim 13, said apparatus further comprising:

means for removing said cryoprotectant from said organ container upon completion of cooling of the organ or tissue.

15. Apparatus according to claim 10, further comprising means for cooling the vitrifiable organ or tissue to a temperature of about −140° C.

16. Apparatus according to claim 10, wherein the first and second means include an organ or tissue flow path and the apparatus further comprises means to purge stagnant cryoprotectant from the organ or tissue flow path to avoid perfusion of the organ or tissue with said stagnant cryoprotectant.

17. The apparatus accordingly to claim 10, further comprising means for immersing the organ or tissue in pre-cooled cryogen to lower the organ or tissue temperature to near its glass transition temperature.

18. Apparatus for equilibrating organs or tissues with vitrifiable concentrations of cryoprotectant, comprising:

a container for holding a biological organ or tissue;

first means for introducing high but not vitrifiable concentrations of cryoprotectant into said container at a temperature of approximately 0° C.; and second means for subsequently introducing fully vitrifiable concentrations of cryoprotectant at a temperature of approximately −10° C. or lower after a predetermined period of immersion cooling of the organ or tissue without perfusion, wherein the first and second means include a flow path and the apparatus further comprises means to purge stagnant perfusate from the flow path to avoid perfusion of the organ or tissue with said stagnant perfusate.

19. Apparatus according to claim 18, further comprising means for removing fully vitrifiable concentration of cryoprotectant from the organ or tissue in a temperature range of between −1° C. and −10° C.

20. Apparatus for equilibrating organs or tissues with vitrifiable concentrations of cryoprotectant, comprising:

a container for holding a biological organ or tissue;

first means for introducing high but not vitrifiable concentrations of cryoprotectant into said container at a temperature of approximately 0° C.;

second means for subsequently introducing fully vitrifiable concentrations of cryoprotectant at a temperature of approximately −10° C. or lower after a predetermined period of immersion cooling of the organ or tissue without perfusion; and means for cooling the vitrifiable organ or tissue to a temperature of about −140° C.

21. A method for equilibrating organs or tissues with vitrifiable concentrations of cryoprotectant, comprising:

placing a biological organ or tissue in a container;

introducing high but not vitrifiable concentrations of cryoprotectant into said container at a temperature of approximately 0° C. through first means;

subsequently introducing fully vitrifiable concentrations of cryoprotectant at a temperature of approximately −10° C. or lower after a predetermined period of immersion cooling of the organ or tissue without perfusion through second means, wherein the first and second means include an organ or tissue flow path; and purging stagnant perfusate from the organ or tissue flow path to avoid perfusion of the organ or tissue with said stagnant perfusate.

22. A method for equilibrating organs or tissues with vitrifiable concentrations of cryoprotectant, comprising placing a biological organ or tissue in a container;

introducing high but not vitrifiable concentrations of cryoprotectant into said container at a temperature of approximately 0° C. through first means;

subsequently introducing fully vitrifiable concentrations of cryoprotectant at a temperature of approximately −10° C. or lower after a predetermined period of immersion cooling of the organ or tissue without perfusion through second means; and, cooling the vitrifiable organ or tissue to a temperature of about −140° C.

23. A method for equilibrating organs or tissues with vitrifiable concentrations of cryoprotectant, comprising:

placing a biological organ or tissue in a container;

introducing through first means high but not vitrifiable concentrations of cryoprotectant into an organ or tissue in said container at a temperature of approximately 0° C. after passing the cryoprotectant through a temperature control means for controlling the temperature thereof;

diverting cryoprotectant from said temperature control means into said container without first passing the cryoprotectant through the organ or tissue to cool the organ or tissue by immersion/conduction;

subsequently introducing through second means fully vitrifiable concentrations of cryoprotectant into the organ or tissue in said container at a temperature of approximately −10° C. or lower after a predetermined period of immersion cooling of the organ or tissue without perfusion via said immersion means; and cooling the fully vitrifiable organ or tissue to a temperature of between −40° C. and −60° C. to vitrify or nearly vitrify the organ or tissue.

\* \* \* \* \*